(12) United States Patent
Tsuji et al.

(10) Patent No.: US 7,273,852 B2
(45) Date of Patent: Sep. 25, 2007

(54) SYNTHETIC C-GLYCOLIPID AND ITS USE FOR TREATING CANCER, INFECTIOUS DISEASES AND AUTOIMMUNE DISEASES

(75) Inventors: Moriya Tsuji, New York, NY (US); Guangwu Chen, Flushing, NY (US); Richard Franck, Riverside, CT (US); Guangli Yang, Forest Hills, NY (US)

(73) Assignee: The Research Foundation of the City University of New York, New York, NY (US)

( * ) Notice: Subject to any disclaimer, the term of this patent is extended or adjusted under 35 U.S.C. 154(b) by 0 days.

(21) Appl. No.: 10/462,211

(22) Filed: Jun. 13, 2003

(65) Prior Publication Data

US 2004/0127429 A1 Jul. 1, 2004

Related U.S. Application Data

(60) Provisional application No. 60/388,862, filed on Jun. 13, 2002.

(51) Int. Cl.
*A61K 31/70* (2006.01)

(52) U.S. Cl. ...................................... 514/23

(58) Field of Classification Search ............... 536/1.11, 536/29.2; 514/23, 25; 424/1.65, 1.73
See application file for complete search history.

(56) References Cited

U.S. PATENT DOCUMENTS

| | | | |
|---|---|---|---|
| 5,780,441 | A | 7/1998 | Higa et al. |
| 5,849,716 | A | 12/1998 | Akimoto et al. |
| 5,936,076 | A | 8/1999 | Higa et al. |
| 6,531,453 | B1 | 3/2003 | Taniguchi et al. |
| 6,635,622 | B2 | 10/2003 | Tomiyama et al. |
| 2002/0032158 | A1 | 3/2002 | Tomiyama et al. |

OTHER PUBLICATIONS

Marcaurelle et al. New Directions in the Synthesis of Glycopeptide Mimetics. Chem. Eur. J., 1999, vol. 5, No. 5, pp. 1384-1390.*
Singh et al. Cutting Edge: Activation of NK T Cells by CD1d and alpha-Galactosylceramide Directes Conventnional T Cells to the Acquisition of a Th2 Phenotype. The Journal of Immunology, 1999, vol. 163, No. 5, pp. 2373-2377.*
Smyth et al. Sequential production of interferon-gamma by NK1. 1+T cells and natural killer cells is essential for the antimetastatic effect of alpha-galactosylceramide. Blood, Feb. 15, 2002, vol. 99, No. 4, 1259-1266.*
Bertozzi et al. Synthesis of C-Glycosides; Stable Mimics of O-Glycosidic Linkages. In Modern methods in Carbohydrate synthesis (Eds. S. H. Khan, R. A. O'Neill), 1996, Harwood Academic Publishers, London, UK, 316-351.*
Bertozzi et al. Carbon-linked galactosphingolipid analogs bind specifically to HIV-1 gp120. J. Am., Chem. Soc. 1992, vol. 114, 10639-10641.*

Michael T. Wilson et al., "Immunotherapy with ligands of natural killer T cells," *Trends in Molecular Medicine* 8, 5: 225-231 (May 2002).
Gloria Gonzalez-Aseguinolaza et al., "Natural Killer T Cell Ligand α-Galactosylceramide Enhances Protective Immunity Induced by Malaria Vaccines," *J. Exp. Med.* 195, 5: 617-624 (Mar. 4, 2002).
Katsuichi Miyamoto et al., "A synthetic glycolipid prevents autoimmune encephalomyelitis by inducing $T_H2$ bias of natural killer T cells," *Nature* 413: 531-534 (Oct. 2001).
Akihiro Shimosaka et al., "KRN7000: A Novel Dendritic Cell Activator." Abstract Book, Instituto Superiore di Sanità, Rome (Oct. 15-17, 2001).
Seokmann Hong et al., "The natural killer T-cell ligand α-galactosylceramide prevents autoimmune diabetes in non-obese diabetic mice," *Nature Medicine* 7, 9: 1052-1056 (Sep. 2001).
Shayan Sharif, "Activation of natural killer T cells by α-galactosylceramide treatment prevents the onset and recurrance of autoimmune Type 1 diabetes," *Nature Medicine* 7: 1057-1062 (Sep. 2001).
Kazuyoshi Kawakami et al., "Activation of Vα14" Natural Killer T Cells by α-Galactosylceramide Results in Development of Th1 Response and Local Host Resistance in Mice Infected with *Cryptococcus neoformans*, *Infection and Immunity* 69: 213-220 (Jan. 2001).
Kazuhiro Kakimi et al., "Natural Killer T Cell Activation Inhibits Hepatitis B Virus Replication In Vivo," *J. Exp. Med.* 192, 7: 921-930 (Oct. 2, 2000).
Gloria Gonzalez-Asequinolaza et al., "α-Galactosylceramide-activated Vα14 natural killer T cells mediate protection against murine malaria," *PNAS* 97, 15: 8461-8466 (Jul. 18, 2000).

(Continued)

*Primary Examiner*—Bruce R. Campell
*Assistant Examiner*—Emily M. Le
(74) *Attorney, Agent, or Firm*—Darby & Darby

(57) ABSTRACT

The invention is directed to compounds of formula (I)

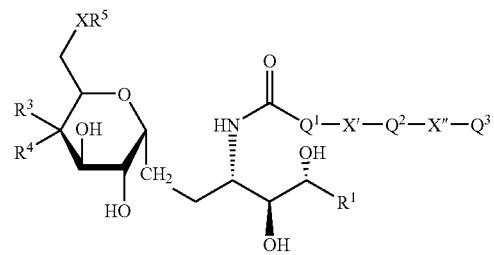

wherein X is O or NH; R' is a hydrocarbon chain; $R^3$ and $R^4$ are hydrogen, OH or a monosaccharide; $R^5$ is hydrogen or a monosaccharide; Q' is optionally present and may be a $C_{1-10}$ hydrocarbon; X' is optionally present and may be O, S or $NR^8$; and $Q^3$ may be a hydrocarbon or hydrogen. The invention is also directed to the use of the compounds for treating cancer, infectious diseases and autoimmune diseases. The invention is also directed to syntheses of the compounds of formula (I).

9 Claims, 8 Drawing Sheets

OTHER PUBLICATIONS

Takashi Nishimura et al., "The interface between innate and acquired immunity: glycolipid antigen presentation by CD1d-expressing dendritic cells to NKT cells induces the differentiation of antigen-specific cytotoxic T lymphocytes," *International Immunology* 12, 7: 987-994 (2000).

Tetsu Kawano et al., "Antitumor Cytotoxicity Mediated by Ligand-activated Human Vα24 NK5 Cells," *Cancer Research* 59: 5102-5105 (Oct. 15, 1999).

Junqing Cui, "Inhibition of T Helper Cell Type 2 Cell Differentiation and Immunoglobulin E Response by Ligand-activated Vα14 Natural Killer T Cells," *J. Exp. Med.* 190, 6: 783-792 (Sep. 20, 1999).

Nagendra Singh et al., "Cutting Edge: Activation of NK T Cells by CD1d and α-Galactosylceramide Directs Conventional T Cells to the Acquisition of a Th2 Phenotype," *The Journal of Immunology*: 2373-2377 (1999).

Nakagawa et al. "Treatment of Hepatic Metasis of the Colon 26 Adenocarcinoma with an α-Galactosylceramide, KRN7000," *Cancer Research* 58: 1202-1207 (Mar. 15, 1998).

Eiichi Kobayashi et al., "KRN7000, A Novel Immunomodulator, and Its Antitumor Activities," *Oncology Research* 7: 529-534 (1995).

Akira Hasegawa et al., "Synthesis of cerebroside, lactosyl ceramide, and ganglioside GM, analogs containing β-thioglycosidically linked ceramide," *Carbohydrate Research* 214: 43-53 (1991).

Soichiro Ishihara et al., "α-Glycosylceramides Enhance the Antitumor Cytotoxicity of Hepatic Lymphocytes Obtained from Cancer Patients by Activating CD3⁻CD56⁺ NK Cells In Vitro," *The Journal of Immunology*, 165:1659-1664 (2000).

Hidemitsu Kitamura et al., "The Natural Killer T (NKT) Cell Ligand α-Galactosylceramide Demonstrates Its Immunopotentiating Effect by Inducing Interleukin (IL)-12 Production by Dendritic Cells and IL-12 Receptor Expression on NKT Cells," *J. Exp. Med.* 189(7):1121-1127 (Apr. 5, 1999).

Tsuji, M., "Glycolipids and phospholipids as natural CD1d-binding NKT cell ligands", Cell. Mol. Life Sci., 2006, 63:1889-1898, Birkhäuser Verlag, Basel, 2006.

"Glycolipid α-C-galactosylceramide is a distinct inducer of dendritic cell function during innate and adaptive immune responses of mice," Fujii et al., Proc. Natl. Academy of Sciences of the USA, 2006, 103(30): 11252-11257 (2006 by the National Academy of Sciences of the USA).

"Stereoselective Synthesis and Immunogenic Activity of the C-Analogue of Sulfatide," Modica et al., Organic Letters, 2006, 8(15): 3255-3258 (American Chemical Society 2006).

Definitions of $T_H1$ Cells and $T_H2$ Cells, Illustrated Dictionary of Immunology, p. 292, Cruse et al. eds. CRC Press, Inc. 1995.

"Modulation of Cd1d-restricted NKT cell responses by using N-acyl variants of α-galactosylceramides," Yu et al., Proc. Natl. Academy of Sciences of the USA, 2005, 102(9), 3383-3388 (2005 by the National Academy of Sciences of the USA).

"Two types of Murine Helper T Cell Clone, I. Definitions according to profiles of lymphokine activities and secreted proteins," Mosmann, et al., The Journal of Immunology, 1996 136(7), 2348-2357 (1986) by the American Association of Immunologists).

"A synthetic glycolipid prevents autoimmune encephalomeyelitis by inducing $T_H2$ bias of natural killer T cells," Miyamoto et al., Letters to Nature 2001, vol. 413, 2001 531-534 (2001 MacMillan Magazines Ltd.).

"Helper T Cells and lymphocyte Activation," Molecular Biology of the Cell, 4th ed., Ch. V(24), Alberts et al., eds., New York and London: Garland Science; 2002 available on-line at.

* cited by examiner

Wild-Type Mice

CD1d-Deficient Mice

Jα18-Deficient Mice

IFN-γ-Deficient Mice

IFN-γ-Receptor Deficient Mice

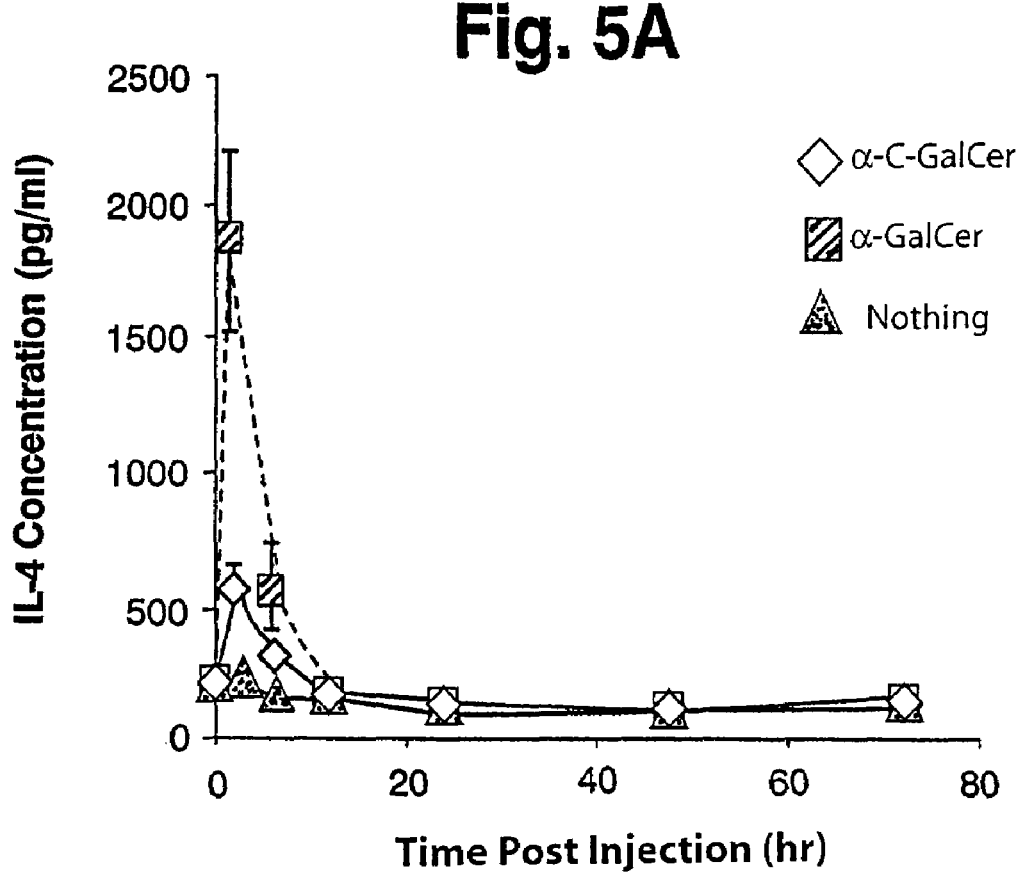

Wild-Type Mice

IL-12-Deficient Mice

SYNTHETIC C-GLYCOLIPID AND ITS USE FOR TREATING CANCER, INFECTIOUS DISEASES AND AUTOIMMUNE DISEASES

This application claims priority under 35 U.S.C. 119(e) from U.S. Provisional Application Ser. No. 60/388,862, filed Jun. 13, 2002, which is incorporated herein by reference in its entirety.

This invention was made with government support under grant number R21 A147840-01A1, awarded by the National Institute of Health/National Institute of Allergy and Infectious Diseases, and grant number R01 GM 60271, awarded by the National Institute of Health/General Medical Sciences. Accordingly, the United States Government has certain rights in the invention.

FIELD OF THE INVENTION

The invention is directed to novel synthetic C-glycolipids, which are useful in treating cancer, infectious diseases and autoimmune diseases. Specifically, the invention is directed to novel synthetic analogs of α-C-galactosylceramides, which are potent mediators of Natural killer T cells, and to methods of making the novel synthetic analogs.

BACKGROUND OF THE INVENTION

Natural killer T (NKT) cells are lymphoid cells which are distinct from mainstream T cells, B cells and NK cells (Arase et al., 1992, *Proc. Nat'l Acad. Sci. USA*, 89:6506; Bendelac et al., 1997, *Annu. Rev. Immunol.*, 15:535). These cells are characterized by co-expression of NK cell receptors and semi-invariant T cell receptors (TCR) encoded by Vα14 and Jα281 gene segments in mice and Vα24 and JαQ gene segments in humans. The activation of NKT cells in vivo promptly induces a series of cellular activation events leading to the activation of innate cells such as natural killer (NK) cells and dendritic cells (DC), the activation of adaptive cells such as B cells and T cells, the induction of co-stimulatory molecules and the abrupt release of cytokines such as interleukin-4 (IL-4) and interferon-γ (IFN-γ) (Burdin et al., *Eur. J. Immunol.* 29: 2014-2025, 1999; Carnaud et al., *J. Immunol.*, 163: 4647-4650, 1999; Kitamura et al., *J. Exp. Med.*, 189: 1121-1128, 1999; Kitamura et al., *Cell Immunol.*, 199: 37-42, 2000; Aderem et al., *Nature*, 406: 782-787, 2000). In addition, activated NKT cells can themselves bring about killing mediated by Fas and perforin. The full activation cascade can be recruited by the engagement of NKT TCR. Alternatively, powerful T-helper-cell type 1 (Th1) functions can be selectively triggered by cytokines such as interleukin-12 (IL-12) released by infected macrophages or DC. These functions are believed likely to be correlated with the important role of NKT cells in conditions such as autoimmune diabetes, rejection of established tumours or the prevention of chemically induced tumours (Yoshimoto et al., 1995, *Science*, 270: 1845; Hammond et al., *J. Exp. Med.*, 187: 1047-1056, 1998; Kawano et al., 1998, *Proc. Natl. Acad. Sci. USA*, 95: 5690; Lehuen et al., *J. Exp. Med.*, 188: 1831-1839, 1998; Wilson et al., *Nature*, 391: 177-181, 1998; Smyth et al., *J. Exp. Med.*, 191: 661-668, 2000). Finally, NKT cells are thought to contribute to antimicrobial immunity through their capacity to influence the Th1-Th2 polarization (Cui et al., *J. Exp. Med.*, 190: 783-792, 1999; Singh et al., *J. Immunol.*, 163: 2373-2377, 1999; Shinkai et al., *J. Exp. Med.*, 191: 907-914, 2000). These cells are therefore implicated as key effector cells in innate immune responses. However, the potential role of NKT cells in the development of adaptive immune responses remains unclear.

Glycolipids are molecules typically found in plasma membranes of animal and plant cells. Glycolipids contain an oligosaccharide which is bonded to a lipid component. Sphingoglycolipids are complex glycolipids which contain ceramide as the lipid component. One class of sphingoglycolipids is alpha-galactosylceramides (α-GalCer), which contain D-galactose as the saccharide moiety, and ceramide as the lipid moiety. α-GalCer is a glycolipid originally extracted from Okinawan marine sponges (Natori et al., *Tetrahedron*, 50: 2771-2784, 1994).

It has been demonstrated that α-GalCer can activate NTK cells both in vitro and in vivo. α-GalCer has been shown to stimulate NK activity and cytokine production by NKT cells and exhibit potent antitumor activity in vivo (Kawano et al., 1997, *Science* 278: 1626-9; Kawano et al. 1998, supra; Kitamura et al. 1999, supra). Kitamura et al. (1999, supra) demonstrated that the immunostimulating effect of α-GalCer was initiated by CD40-CD40L-mediated NKT-DC interactions. As the immunoregulatory functions of α-GalCer were absent in both CD1d-1- and NKT-deficient mice, this indicates that α-GalCer has to be presented by the MHC class I-like molecule CD1d.

CD1 is a conserved family of non-polymorphic genes related to MHC that seems to have evolved to present lipid and glycolipid antigens to T cells and in this way participates in both an innate and an adaptive pathway of antigen recognition (reviewed by Park et al., *Nature*, 406: 788-792, 2000; see also Calabi et al., *Eur. J. Immunol.*, 19: 285-292, 1989; Porcelli et al., *Annu. Rev. Immunol.*, 17: 297-329, 1999). The CD1 family comprises up to five distinct genes (isotypes) that can be separated into two groups on the basis of sequence homology. Group 1, which comprises CD1a, CD1b, CD1c and CD1e, is present in humans but absent from mouse and rat. Group 2, which includes CD1d, is found in all species studied so far, including humans.

CD1 isotypes are expressed selectively by antigen-presenting cells such as dendritic cells (DCs), macrophages and subsets of B cells, but apart from CD1d expression in hepatocytes they are generally not expressed in solid tissues (Porcelli et al., supra; Bendelac et al., *Annu. Rev. Immunol.*, 15: 535-562, 1997).

α-GalCer is recognized in picomolar concentrations by mouse and human CD1d-restricted lymphocytes that express a semi-invariant TCR and exert potent effector and regulatory functions (Kawano et al., 1997, supra). CD1d/α-GalCer complex is, in turn, recognized by the antigen receptors of mouse Vα14 and human Vα24 natural killer T (NKT) cells (Bendelac et al., *Science*, 268: 863-865, 1995; Bendelac et al., *Annu. Rev. Immunol.*, 15: 535-562, 1997; Park et al., *Eur. J. Immunol.*, 30: 620-625, 2000).

α-GalCer has been demonstrated to activate murine NKT cells both in vivo and in vitro, upon binding to CD1d (Kawano et al., 1997, supra; Burdin et al., 1998, *J. Immunol.*, 161:3271-3281), and in human NKT cells in vitro (Spada et al., 1998, *J. Exp. Med.*, 188:1529-1534; Brossay et al., 1998, *J. Exp. Med.* 188:1521-1528). For example, α-GalCer was shown to display NKT-mediated anti-tumor activity in vitro by activating human NKT cells (Kawano et al., 1999, *Cancer Res.*, 59:5102-5105).

In addition to α-GalCer, other glycosylceramides having α-anomeric conformation of sugar moiety and 3,4-hydroxyl groups of the phytosphingosine (such as α-glucosylceramide [α-GlcCer], Galα1-6Galα1-1'Cer, Galα1-6Glcα1-1'Cer, Galα1-2Galα1-1'Cer, and Galβ1-3Galα1-1'Cer) have been demonstrated to stimulate proliferation of Vα14 NKT cells in mice, although with lower efficiency (Kawano et al., *Science*, 278: 1626-1629, 1997, supra). By testing a panel of α-GalCer analogs for reactivity with mouse Vα14 NKT cell hybridomas, Brossay et al. (*J. Immunol.*, 161: 5124-5128, 1998) determined that nearly complete truncation of the α-GalCer acyl chain from 24 to 2 carbons does not significantly affect the mouse NKT cell response to glycolipid presented by either mouse CD1 or its human homolog.

It has been also demonstrated that in vivo administration of α-GalCer not only causes the activation of NKT cells to induce a strong NK activity and cytokine production (e.g., IL-4, IL-12 and IFN-γ) by CD1d-restricted mechanisms, but also induces the activation of immunoregulatory cells involved in acquired immunity (Nishimura et al., 2000, *Int. Immunol.*, 12: 987-994). Specifically, in addition to the activation of macrophages and NKT cells, it was shown that in vivo administration of α-GalCer resulted in the induction of the early activation marker CD69 on CD4+ T cells, CD8+ T cells, and B cells (Burdin et al., 1999, *Eur. J. Immunol.* 29: 2014; Singh et al., 1999, *J. Immunol.* 163: 2373; Kitamura et al., 2000, *Cell. Immunol.* 199:37; Schofield et al., 1999, *Science* 283: 225; Eberl et al., 2000, *J. Immunol.*, 165:4305-4311).

Various α-GalCer compounds have been shown in the prior art. U.S. Pat. No. 5,780,441 describes mono- and di-glycosylated α-GalCer compounds of the following structure:

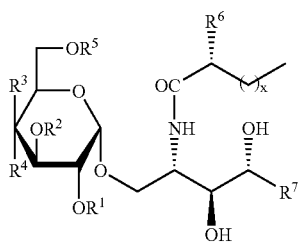

wherein $R^1$ is H or

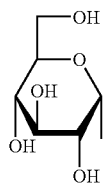

$R^2$ is H,

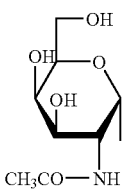 or 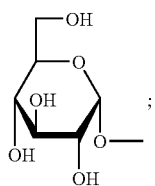 ;

$R^3$ and $R^6$ are H or OH, respectively,
$R^4$ is H, OH or

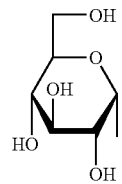

$R^5$ is H or

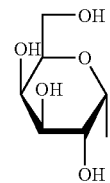

x is an integer from 19 to 23; and
$R^7$ is $-(CH_2)_{11}-CH_3$, $-(CH_2)_{12}-CH_3$, $-(CH_2)_{13}-CH_3$, $-(CH_2)_9-CH(CH_3)_2$, $-(CH_2)_{10}-CH(CH_3)_2$, $-(CH_2)_{11}-CH(CH_3)_2$, $-(CH_2)_{11}-CH(CH_3)-C_2H_5$, wherein at least one of $R^1$, $R^2$, $R^4$ and $R^5$ is a glycosyl moiety.

The compounds are disclosed for use as antitumor agents, as bone marrow cell-proliferation treating agents, and as immunostimulating agents.

Recently, α-GalCer molecules have also been shown to have activity against viral diseases. Kakimi, *J. Exp. Med.* 192: 921-930 (2000) discloses that natural killer (NKT) cells in the liver of hepatitis B virus (HBV) transgenic mice were activated by a single injection of α-GalCer, thereby inhibiting HBV replication. α-GalCer has also been shown to be effective against microbial infections. Gonzalez-Asequinaloza, *Proc. Natl. Acad. Sci.* USA 97: 8461-8466 (2000) discloses that the administration of α-GalCer inhibits the development of malaria parasites, resulting in strong antimalaria activity.

α-GalCer has also demonstrated inhibition of the onset and recurrence of autoimmune type I diabetes. Sharif, *Nature Medicine* 7: 1057-1062 (2001) demonstrates that activation of NKT cells by α-GalCer protects mice from type I diabetes and prolongs the survival of pancreatic islets transplanted into newly diabetic mice. See also Hong, *Nature Medicine* 9: 1052-1056 (2001). Sharif also demonstrated that when administered after the onset of insulitis, α-GalCer and IL-7 displayed a synergy, which is believed to be due to the ability of IL-7 to render NKT cells fully responsive to α-GalCer.

α-GalCer has also demonstrated antifungal activity. Kawakami, *Infection and Immunity* 69: 213-220 (2001) demonstrates that upon administration to mice, α-GalCer increased the serum level of gamma interferon, resulting in inhibition of the fungal pathogen *Cryptococcus neoformans*.

α-GalCer analogs have also demonstrated effectiveness against autoimmune diseases. Miyamoto, *Nature* 413: 531-534 (2001) describes use of α-GalCer analogs which induce TH2 bias of autoimmune T cells by causing natural killer T (NKT) cells to produce IL-4, leading to suppression of experimental autoimmune encephalomyelitis.

A synthetic analog of α-GalCer, KRN 7000 (2S,3S,4R)-1-O-(α-D-galactopyranosyl)-2-(N-hexacosanoylamino)-1,3,4-octadecanetriol, can be obtained from Pharmaceutical Research Laboratories, Kirin Brewery (Gumna, Japan) or synthesized as described in Morita et al., *J. Med. Chem.*, 1995, 38: 2176-2187.

KRN 7000 has the structure:

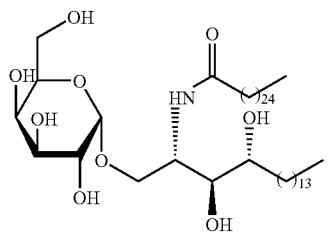

KRN 7000 has been shown to display activity against tumors in mice. Kobayashi, et al., *Oncol. Res.* 7:529-534 (1995). In particular, KRN 7000 has been shown to be effective in preventing cancer metastasis. See, e.g., Nakagawa, *Canc. Res.* 58, 1202-1207 (1998) (KRN 7000 effective in treating liver metastasis of adenocarcinoma colon 26 cells in mice). KRN 7000 is also described in Kobayashi et al., 1995, *Oncol. Res.*, 7:529-534, Kawano et al., 1997, *Science*, 278:1626-9, Burdin et al., 1998, *J. Immunol.*, 161:3271, and Kitamura et al., *J. Exp. Med.*, 1999, 189: 1121, and U.S. Pat. No. 5,936,076.

Importantly, in addition to its ability to stimulate immune responses, recent human trials have shown that α-GalCer is not cytotoxic in humans. See Shimosaka et al. Cell Therapy: Filling the gap between basic science and clinical trials, First Int'l Workshop 2001, abstract pp. 21-22. Other studies have demonstrated that α-GalCer, independently of its dosage, does not induce toxicity in rodents and monkeys (e.g., Nakagawa et al., 1998, *Cancer Res.*, 58: 1202-1207), although a recent study showed the transient elevation of liver enzyme activities immediately after α-GalCer treatment in mice, suggesting a minor liver injury (Osman et al., 2000, *Eur. J. Immunol.*, 39: 1919-1928).

However, most mammals, including humans, have abundant amount of α-galactosidase, an enzyme which digests α-GalCer by catalyzing the degradation of α-D-galactoside bonds. As a result, α-GalCer has a short half-life, and therefore its in vivo therapeutic effect may be reduced.

Recently, it has been shown that the activity of α-GalCer can be modified through formation of a truncated sphingosine chain. The modified α-GalCer is effective in treating autoimmune encephalomyelitis in mice. Miyamato et al., *Nature* 413:531-534 (2001).

Applicants have now discovered α-GalCer analogs which have improved stability in vivo over α-GalCer.

Applicants have also discovered α-GalCer analogs which have improved therapeutic efficacy over α-GalCer.

OBJECTS OF THE INVENTION

It is an object of the invention to form compounds having the pharmacological activity of α-GalCer, and resistance to α-galactosidase, resulting in improved stability in vivo.

It is also an object of the invention to form novel compounds for treating cancers, infectious diseases and autoimmune diseases.

SUMMARY OF THE INVENTION

This invention is directed to novel C-glycolipid compounds of formula (I)

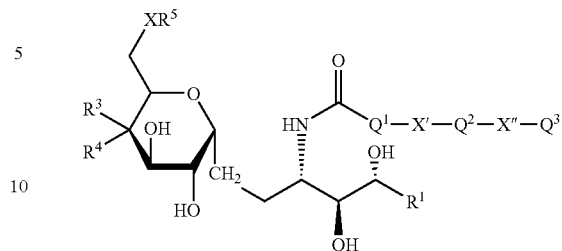

wherein X is O or NH;

$R^1$ is selected from the group consisting of $-(CH_2)_{11}CH_3$, $-(CH_2)_{12}CH_3$, $-(CH_2)_{13}CH_3$, $-(CH_2)_9CH(CH_3)_2$, $-(CH_2)_{10}CH(CH_3)_2$, $-(CH_2)_{11}CH(CH_3)_2$ and $(CH_2)_{11}CH(CH_3)-C_2H_5$;

$R^3$ is OH or a monosaccharide and $R^4$ is hydrogen, or $R^3$ is hydrogen and $R^4$ is OH or a monosaccharide;

$R^5$ is hydrogen or a monosaccharide;

$Q^1$ is optionally present and is a $C_{1-10}$ straight or branched chain alkylene, alkenylene, or alkynylene;

X' is optionally present and is O, S or $NR^8$;

$Q^2$ is optionally present and is a $C_{1-10}$ straight or branched chain alkylene, alkenylene or alkynylene;

X" is optionally present and is O, S or $NR^8$;

$Q^3$ is a straight or branched chain $C_{1-10}$ alkyl, alkenyl or alkynyl, or is hydrogen, wherein each $Q^1$, $Q^2$ or $Q^3$ is optionally substituted with hydroxyl, halogen, cyano, nitro, $SO_2$, $NHR^8$, or $C(=O)-R^9$; and wherein $R^8$ is hydrogen, $C_{1-5}$ alkyl, $C_{1-5}$ alkoxy, halogen, cyano, nitro, $SO_2$ or $C(=O)-R^9$;

$R^9$ is hydrogen, $C_{1-5}$ alkyl, $C_{1-5}$ alkoxy or $NHR^{10}$;

$R^{10}$ is hydrogen, $C_{1-5}$ alkyl or $C_{1-5}$ alkoxy;

and pharmaceutically acceptable salts or esters thereof.

A preferred compound of formula (I) is 3'S,4'S,5'R-3'-hexacosanoyl-4,5'-di-O-acetylnonadecyl-2,3,4,6-tetra-O-acetyl-α-C-D-galactopyranoside (wherein X is O, $R^3$ is OH, $R^4$ and $R^5$ are hydrogen, $R^1$ is $-(CH_2)_{13}CH_3$, $Q^1$-X'-$Q^2$-X"-$Q^3$ is $-(CH_2)_{24}-CH_3$, which is also known as CRONY-101.

The invention is also directed to prodrugs and pharmaceutically acceptable salts of the compounds described, and to pharmaceutical compositions suitable for different routes of drug administration comprising a therapeutically effective amount of a described compound of the invention admixed with a pharmaceutically acceptable carrier.

The invention is also directed to methods of treating a disease selected from the group consisting of cancers, autoimmune diseases and infectious diseases (including HIV and Hepatitis C virus).

The invention is also directed to pharmaceutical compositions comprising the compounds disclosed above, as well as methods of using these compositions to treat cancer, infectious diseases and autoimmune diseases.

The invention is also directed to methods of inducing the production of Th1 type cytokines, such as IFN-γ and IL-12, in a mammal in need thereof, by administering to the mammal a therapeutically effective amount of a compound of claim 1. In preferred embodiments, the mammal is a human.

The invention is also directed to novel intermediate compounds of formula (II)

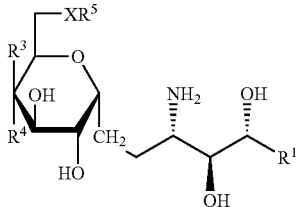

(II)

wherein

X is O or NH;

$R^3$ is OH or a monosaccharide and $R^4$ is hydrogen, or $R^3$ is hydrogen and $R^4$ is OH or a monosaccharide;

$R^5$ is hydrogen or a monosaccharide; and $R^1$ is selected from the group consisting of —$(CH_2)_{11}CH_3$, —$(CH_2)_{12}CH_3$, —$(CH_2)_{13}CH_3$, —$(CH_2)_9CH(CH_3)_2$, —$(CH_2)_{10}CH(CH_3)_2$, —$(CH_2)_{11}CH(CH_3)_2$ and $(CH_2)_{11}CH(CH_3)$—$C_2H_5$;

and salts or esters thereof.

A preferred embodiment of formula (II) is the novel intermediate compound 3'S,4'S,5'R,3'-amino-4,5'-di-O-acetylnonadecyl-2,3,4,6-tetra-O-acetyl-α-C-D-galactopyranoside, which is used as a scaffold for the introduction of acyl chains C(=O)-Q'-X'-Q²-X"-Q³ in the synthesis of compounds of formula (I).

The invention is also directed to a method of synthesizing a C-glycolipid compound of formula (I) by acylating a compound of formula (II) at the amino nitrogen.

The invention is also directed to novel intermediate compounds of formula

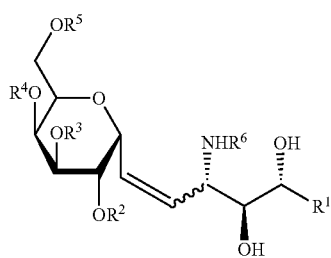

(III)

wherein $R^1$ is selected from the group consisting of —$(CH_2)_{11}CH_3$, —$(CH_2)_{12}CH_3$, —$(CH_2)_{13}CH_3$, —$(CH_2)_9CH(CH_3)_2$, —$(CH_2)_{10}CH(CH_3)_2$, —$(CH_2)_{11}CH(CH_3)_2$ and $(CH_2)_{11}CH(CH_3)$—$C_2H_5$;

$R^2$, $R^3$, $R^4$ and $R^5$ are each independently selected from the group consisting of alkyl, aryl, alkylaryl and trialkylsilyl;

$R^6$ is selected from the group consisting of alkyl, aryl, alkylaryl, trialkylsilyl, —C(=O)—O-alkyl, —C(=O)—O-aryl and —C(=O)—O-alkylaryl;

or a salt or ester thereof.

Preferred compounds are those wherein each of $R^2$, $R^3$, $R^4$ and $R^5$ are alkylaryl, for example benzyl or 4,6-benzylidene. Also preferred are compounds wherein $R^6$ is benzyloxycarbonyl.

A preferred embodiment of formula (III) is the novel intermediate compound 1-(2',3',4',6'-tetra-O-benzyl-α-D-galactopyranosyl)-3-benzyloxycarbonylamino-1-nonadecene-4,5-diol.

The invention is also directed to a method of synthesizing a C-glycolipid compound of formula (I) wherein X is O, $R^3$ is OH and $R^4$ is hydrogen, and $R^5$ is hydrogen, from a compound of formula (III), which is subjected to reduction of the carbon-carbon double bond and deprotection of the amine and the sugar hydroxyl groups to form a compound of formula (II), which may be used as a scaffold for the introduction of acyl chains C(=O)-Q'-X'-Q²-X"-Q³ at the amino nitrogen.

The invention is also directed to a method of synthesizing a C-glycolipid compound of formula (I) wherein X is O, $R^3$ is OH, $R^4$ is hydrogen, and $R^5$ is hydrogen, by reacting a compound of formula (IV)

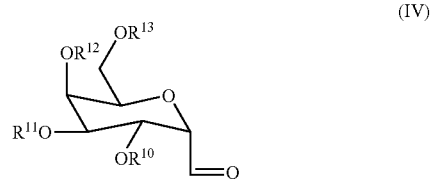

(IV)

wherein each of $R^{10}$, $R^{11}$, $R^{12}$ and $R^{13}$ is independently selected from alkyl, aryl, alkylaryl or trialkylsilyl;

with a compound of formula V

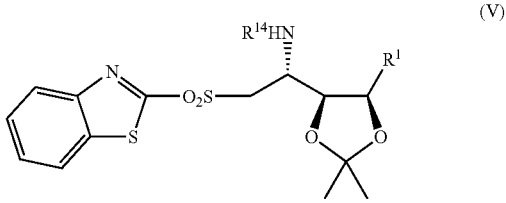

(V)

wherein $R^{14}$ is selected from alkyl, aryl, alkylaryl, trialkylsilyl, —C(=O)—O-alkyl, —C(=O)—O-aryl or —C(=O)—O-alkylaryl; and wherein $R^1$ is selected from the group consisting of —$(CH_2)_{11}CH_3$, —$(CH_2)_{12}CH_3$, —$(CH_2)_{13}CH_3$, —$(CH_2)_9CH(CH_3)_2$, —$(CH_2)_{10}CH(CH_3)_2$, —$(CH_2)_{11}CH(CH_3)_2$ and $(CH_2)_{11}CH(CH_3)$—$C_2H_5$;

to form a compound of formula (VI)

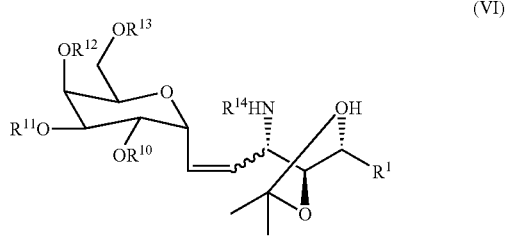

(VI)

and subjecting the compound of formula (VI) to
(a) deisopropylidenation to remove the ring structure;
(b) reduction of the C—C double bond; and
(c) deprotection of the sugar hydroxyl groups, thereby forming the compound of formula (II), which may be used as a scaffold for the introduction of acyl chains C(=O)-Q'-X'-Q²-X"-Q³ in the synthesis of compounds of formula (I).

DETAILED DESCRIPTION OF THE INVENTION

Figure 1A:
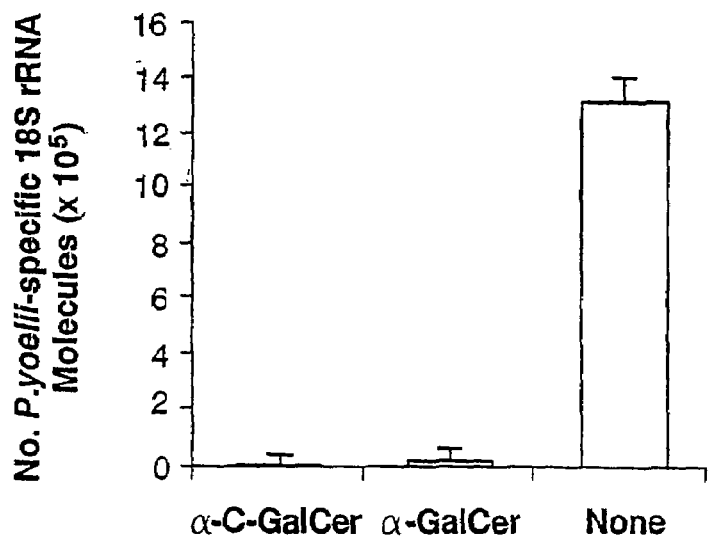
FIG. 1(A) is a bar graph showing malaria liver stage development in wild type BALB/c mice treated intraperitoneally with 2 μg of α-C-GalCer, α-GalCer, or nothing two days before challenge with live P. yoelii sporozoites.

α-Galactosylceramide (α-GalCer) is a glycolipid ligand for natural killer T (NKT) cells, which respond to the glycolipid and produce both interferon (IFN)-γ and interleukin (IL)-4. The production of large amounts of both cytokines, which possess opposite biological effects, i.e. Th1- and Th2-type response, hampers α-GalCer from executing either desired effect. It has now been discovered that synthetic C-glycoside analogs of α-GalCer of general formula (I) act as an NKT cell ligand and display 100-1000 fold higher activity against tumor and malaria, by preferentially inducing the production of Th1-type cytokines, IFN-γ and IL-12, in vivo. Administration of the α-C-GalCer to mice consistently resulted in not only prolonged production of the Th1-type cytokines, but also decreased population of the Th2 cytokine, IL-4, as compared to α-GalCer. In two disease models requiring Th1-type responses for control, namely malaria and melanoma metastases, α-C-GalCer exhibited a 1000-fold and 100-fold more potent activity, respectively, than α-GalCer.

Definitions

The term "monosaccharide" means a sugar molecule having a chain of 3-10 carbon atoms in the form of an aldehyde (aldose) or ketone (ketose). Suitable monosaccharides contemplated for use in the invention include both naturally occurring and synthetic monosaccharides. Sample monosaccharides include trioses, such as glycerose and dihydroxyacetone; textroses such as erythrose and erythrulose; pentoses such as xylose, arabinose, ribose, xylulose ribulose; methyl pentoses (6-deoxyhexoses), such as rhamnose and fucose; hexoses, such as glucose, mannose, galactose, fructose and sorbose; and heptoses, such as glucoheptose, galamannoheptose, sedoheptulose and mannoheptulose. Preferred monosaccharides are hexoses.

An "effective amount" of the compound for treating a disease, e.g., a cancer, an infectious disease or an autoimmune disease, is an amount that results in measurable amelioration of at least one symptom or parameter of the disease in mammals, including humans.

The term "prodrug" as used herein refers to any compound that may have less intrinsic activity than the active compound or "drug" but when administered to a biological system generates the active compound or "drug" substance either as a result of spontaneous chemical reaction or by enzyme catalyzed or metabolic reaction.

As used herein, the term "pharmaceutically acceptable salts, esters, amides, and prodrugs" refer to those salts (e.g., carboxylate salts, amino acid addition salts), esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

The terms "treatment" or "treating" include prophylactic or therapeutic administration of compounds of the invention, for the cure or amelioration of disease or symptoms associated with disease, and includes any benefits obtained or derived from the administration of the described compounds.

The term "therapeutically effective" applied to dose or amount refers to that quantity of a compound or pharmaceutical composition that is sufficient to result in a desired activity upon administration to a mammal in need thereof.

The terms "pharmaceutically acceptable" and "physiologically acceptable" are used interchangeably, and as used in connection with compositions of the invention refer to molecular entities and other ingredients of such compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" applied to pharmaceutical compositions of the invention refers to a diluent, excipient, or vehicle with which a compound of the invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution, saline solutions, and aqueous dextrose and glycerol solutions are preferably used as carriers, particularly for injectable solutions. Suitable pharmaceutical carriers are described in "Remington's Pharmaceutical Sciences" by E. W. Martin, 18th Edition.

Therapeutic Uses

In one embodiment, the compounds of the invention are useful for the treatment of cancer, e.g. as anti-tumor agents for inhibiting the growth of tumors, and for treatment of cell proliferative disorders. The compounds of the invention may be used alone, or in combination with chemotherapy or radiotherapy.

More specifically, the compounds of the invention are useful in the treatment of a variety of cancers including, but not limited to carcinoma such as bladder, breast, colon, kidney, liver, lung, including small cell lung cancer, non-small cell lung cancer, esophagus, gall bladder, ovary, pancreas, testicular, stomach, renal, liver, cervix, thyroid, prostate, and skin, including squamous cell carcinoma; hematopoietic tumors of lymphoid lineage, including leukemia, acute lymphocitic leukemia, acute lymphoblastic leukemia, B cell lymphoma, T cell lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma.

Cell proliferative disorders for which the compounds are useful include benign prostate hyperplasia, familial adenomatosis polyposis, neuro fibromatosis, psoriasis, vascular smooth cell proliferation associated with atherosclerosis, pulmonary fibrosis, arthritis glomerulonephritis and post-surgical stenosis and restenosis.

In another embodiment, the compounds of the invention are also useful for treating infectious diseases, including parasitic, fungal, yeast, bacterial, mycoplasmal and viral diseases (where a particular class of cells can be identified as harboring the infective entity).

For example, the compounds may be useful in treating infections from a human papilloma virus, a herpes virus such as herpes simplex or herpes zoster, a retrovirus such as human immunodeficiency virus 1 or 2, a hepatitis virus (hepatitis A virus (HAV)), hepatitis B virus (HBV) non-A, blood borne (hepatitis C) and other enterically transmitted hepatitis (hepatitis E), and HBV associated delta agent (hepatitis D)), influenza virus, rhinovirus, respiratory syncytial virus, cytomegalovirus, adenovirus, *Mycoplasma pneumoniae*, a bacterium of the genus *Salmonella, Staphylococcus, Streptococcus, Enterococcus, Clostridium, Escherichia, Klebsiella, Vibrio, Mycobacterium, amoeba*, a malarial parasite, *Trypanosoma cruzi*, helminth infections, such as nematodes (round worms) (*Trichuriasis, Enterobiasis, Ascariasis*, Hookworm, *Strongyloidiasis, Trichinosis filariasis*); trematodes (flukes) (*Schistosomiasis, Clonorchiasis*), cestodes (tape worms) (*Echinococcosis, Taeniasis saginata, Cysticercosis*); visceral worms, visceral larva migrans (e.g., *Toxocara*), eosinophilic gastroenteritis (e.g., *Anisaki* spp., *Phocanema* ssp.), cutaneous larva migrans (*Ancylostona braziliense, Ancylostoma caninum*).

In certain preferred embodiments, the compounds of the invention are useful for treating infection with a hepatitis C virus.

In other preferred embodiments, the compounds of the invention are useful for treating human immunodeficiency virus (HIV), and in the prevention of infection by HIV, the treatment of infection by HIV and the prevention and/or treatment of the resulting acquired immune deficiency syndrome (AIDS).

In another preferred embodiment, the compounds of the invention are useful for treating malaria in a mammal (e.g., human) by administration of a compound of the invention.

In other embodiments, the compounds of the invention are useful for treating autoimmune diseases, such as rheumatoid arthritis, psoriatic arthritis, multiple sclerosis, systemic lupus erythematosus, myasthenia gravis, juvenile onset diabetes, glomerulonephritis, autoimmune thyroiditis, Behcet's disease, and other disorders such as Crohn's disease, ulcerative colitis, bullous pemphigoid, sarcoidosis, psoriasis, ichthyosis, Graves ophthalmopathy and asthma.

The subjects to which the present invention is applicable may be any mammalian or vertebrate species, which include, but are not limited to, cows, horses, sheep, pigs, fowl (e.g., chickens), goats, cats, dogs, hamsters, mice, rats, monkeys, rabbits, chimpanzees, and humans. In a preferred embodiment, the subject is a human.

Modes of Administration

Modes of administration of compounds and compositions of the invention include oral and enteral, intravenous, intramuscular, subcutaneous, transdermal, transmucosal (including rectal and buccal), and by inhalation routes. Preferably, an oral or transdermal route is used (i.e., via solid or liquid oral formulations, or skin patches, respectively). In some cases, the compounds can be pulsed with syngeneic dendritic cells, followed by transferring intravenously into patients.

Pharmaceutical Compositions

Solid dosage forms for oral administration of compounds and compositions of the invention include capsules, tablets, pills, powders, granules, and suppositories. In such solid dosage forms, the active compound of the invention can be admixed with at least one inert customary excipient (or carrier) such as sodium citrate or dicalcium phosphate; or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol, and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Such solid compositions or solid compositions that are similar to those described can be employed as fillers in soft- and hard-filled gelatin capsules using excipients such as lactose or milk, sugar as well as high molecular weight polyethyleneglycols, and the like.

Solid dosage forms such as tablets, dragées, capsules, pills, and granules can be prepared with coatings and shells, such as enteric coatings or other suitable coatings or shells. Several such coatings and/or shells are well known in the art, and can contain opacifying agents, and can also be of such composition that they release the active compound or compounds in a certain part of the intestinal tract in a delayed manner. Examples of embedding compositions which can be used are polymeric substances and waxes. The active compounds can also be used in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms can contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like. If desired, the composition can also include adjuvants, such as wetting agents, emulsifying and suspending agents, sweetening, flavoring and/or perfuming agents.

The composition may include a carrier, as defined herein. Suitable carriers include macromolecules which are soluble in the circulatory system and which are physiologically acceptable, as defined herein. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

Suspensions, in addition to the active compounds, can contain suspending agents, such as, ethoxylated isostearyl alcohols, polyoxyethylene sorbitol and sorbitan esters, microcrystalline cellulose, aluminum metahydroxide, bentonite, agar-agar, tragacanth, and the like. Mixtures of suspending agents can be used if desired.

Compositions for rectal administrations are preferably suppositories which can be prepared by mixing the compounds of the present invention with suitable nonirritating excipients or carriers such as cocoa butter, polyethyleneglycol, or a suppository wax which are solid at ordinary temperatures but liquid at body temperature and therefore, melt in the rectum or vaginal cavity and release the active component.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

Dosage forms for topical administration of a compound of the invention include ointments, powders, sprays and inhalants. The active component can be admixed under suitable conditions (e.g., sterile conditions) with a physiologically acceptable carrier and any preservatives, buffers, or propellants as may be required. Ophthalmic formulations, eye ointments, powders, and solutions are also contemplated as being within the scope of this invention.

Effective Dosages

An effective amount for treating the diseases can easily be determined by empirical methods known to those skilled in the art, such as by establishing a matrix of dosages and frequencies of administration and comparing a group of experimental units or subjects to each point in the matrix. The exact amount to be administered to a patient will vary depending on the particular disease, the state and severity of the disease, and the physical condition of the patient. A measurable amelioration of any symptom or parameter can be determined by a physician skilled in the art or reported by the patient to the physician. Clinically significant attenuation or amelioration means perceptible to the patient and/or to the physician.

It will also be understood that the specific dosage form and dose level for any particular patient will depend on a variety of factors including the activity of the specific compound employed; the age, body weight, general health, and sex of the individual being treated; the time and route of administration; the rate of excretion; other drugs which have previously been administered; and the severity of the particular disease undergoing therapy.

The amount of the agent to be administered can range from between about 0.01 to about 25 mg/kg/day, preferably from between about 0.1 to about 10 mg/kg/day and most preferably from between about 0.2 to about 5 mg/kg/day. It will be understood that the pharmaceutical compositions of the present invention need not in themselves contain the entire amount of the agent that is effective in treating the disorder, as such effective amounts can be reached by administration of a plurality of doses of such pharmaceutical compositions.

For example, the compounds of the invention can be formulated in capsules or tablets, each preferably containing 50-200 mg of the compounds of the invention, and are most preferably administered to a patient at a total daily dose of 50-400 mg, preferably 150-250 mg, and most preferably about 200 mg.

Toxicity and therapeutic efficacy compositions containing compounds of the invention can be determined by standard pharmaceutical procedures in experimental animals, e.g., by determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred. While therapeutics that exhibit toxic side effects can be used (e.g., when treating severe forms of cancer or life-threatening infections), care should be taken to design a delivery system that targets such immunogenic compositions to the specific site (e.g., lymphoid tissue mediating an immune response, tumor or an organ supporting replication of the infectious agent) in order to minimize potential damage to other tissues and organs and, thereby, reduce side effects.

As specified above, data obtained from the animal studies can be used in formulating a range of dosage for use in humans. The therapeutically effective dosage of compounds of the present invention in humans lies preferably within a range of circulating concentrations that include the ED50 with little or no toxicity. The dosage can vary within this range depending upon the dosage form employed and the route of administration utilized. Ideally, a single dose should be used.

Synthesis of Compounds of the Invention

In a first method of synthesizing the compounds of the invention, Synthesis A, the compounds may be formed from commercially available starting materials galactose penta acetate (1) and L-homoserine (2), as shown below:

As taught by Kolb et al, 1994, Chem. Rev. 94: 2483, hydroxy groups are introduced into the homosphingosine moiety. As taught in Belica, et al, 1998, Tetrahedron Lett. 39: 8225-8228, Yang et al., 1999, Organic Letters 1: 2149-2151, and Yang, et al, 2001, Organic Letters 3: 197-200, the homosphingosine is linked to the galactose. The alpha configuration is established using the method of Yang, et al., 1999, Organic Letters 1: 2149-2151. The sphingosine is converted to the ceramide using well-established methods.

The compounds of formula (I) may be formed from the compounds of formula (II) by acylating a compound of formula (II) with a reactant $R^x$—C(=O)-Q'X'Q$^2$X"Q$^3$ to add the C(=O)-Q'X'Q$^2$X"Q$^3$ chain at the amino nitrogen position of (II). The acylation of an amino group is well known to chemists skilled in the art of organic synthesis. Suitable reactants include p-nitrophenyl carboxylates, wherein $R^x$ is p-nitrophenyl as taught in Morita et al. J. Med. Chem, 1995, 38: 2176-2187. Alternative $R^x$ groups include o-nitrophenyl, o-N-succinimidyl, chloride, bromide, or mixed anhydrides.

The compounds of formula (II) can be formed from the compounds of formula (III) by reducing the carbon-carbon double bond, and then deprotecting the amine and hydroxyl groups of the sugar moiety Compounds of formula (T) wherein X is NH may be formed according to the methods taught by Savage et al., Org. Lett. 2002 Apr. 18 4(8): 1267-70.

In a second method of synthesizing the compounds of the invention, Synthesis B, a sugar aldehyde, e.g. α-C-galactosyl aldehyde, is coupled with the commercially available compound phytosphingosine. α-C galactosyl aldehyde can be formed by the Bednarski procedure from the starting material methyl galactoside.

The coupling reaction yields a compound of formula III, which is then subjected to cleavage of an isopropylidene group, reduction of the double bond, and deprotection, to yield the compound of formula (II).

EXEMPLARY EMBODIMENTS OF THE INVENTION

The compounds of this invention and their preparation can be understood further by the examples which illustrate some of the processes by which these compounds are prepared or used. Theses examples do not limit the invention. Variations of the invention, now known or further developed, are considered to fall within the scope of the present invention as hereinafter claimed.

1. Synthesis of CRONY-101 by Synthesis A Method

The α-GalCer derivative CRONY-111 may be synthesized according to the following synthesis.

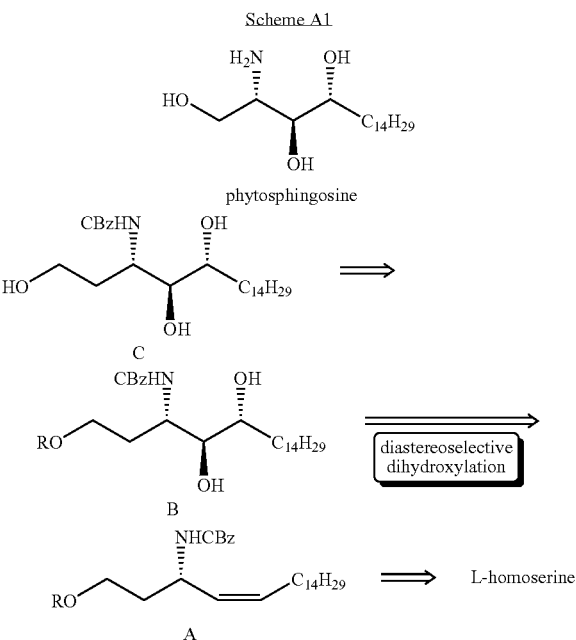

The diastereoselective dihydroxylation of the optically active olefin A, which is readily accessible from L-homoserine, would afford the protected homophytosphingosine derivative B in a stereoselective fashion. The synthetic route from commercially available L-homoserine is shown in Scheme A2.

L-homoserine 1 was converted into methyl ester 2 via two steps in 60% overall yield (Ozinskas, A. et al., J. Org. Chem. 1986, 51, 5047-5050; Shioiri, T. et al., Org. Synth., 1989, 68, 1). After the primary alcohol was protected, the ester was reduced to an aldehyde 3 using diisobutylaluminum hydride (DIBAL) as the reducing reagent. The aldehyde was then coupled to $C_{15}$ long-chain Wittig phosphonium salt using sodium hexamethyldisilazane (NaHMDS) in THF (−75° C.) to give Z-olefin 4 as the only product (Beaulieu, P. L. et al., Org. Chem. 1991, 56, 4196-4204; Imashiro, R. et al, Tetrahedron 1998, 54, 10657-10670). Sharpless dihydroxylation (Sharpless, K. B. et al., J. Org. Chem. 1992, 57, 2768-2771), of the optically active Z-olefin using AD-mix-β gave ca. 7:3 mixture of 3S,4S,5R(5) and 3S,4R,5S(6)dihydroxylated isomers, respectively. Their relative and absolute configurations were confirmed by comparison of NMR data of their cyclic carbamate derivatives.

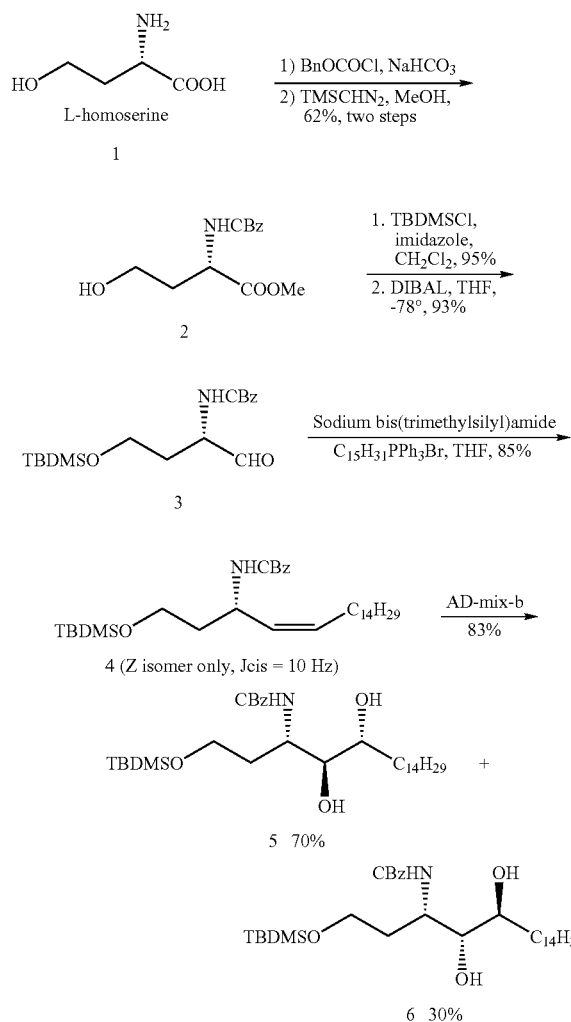

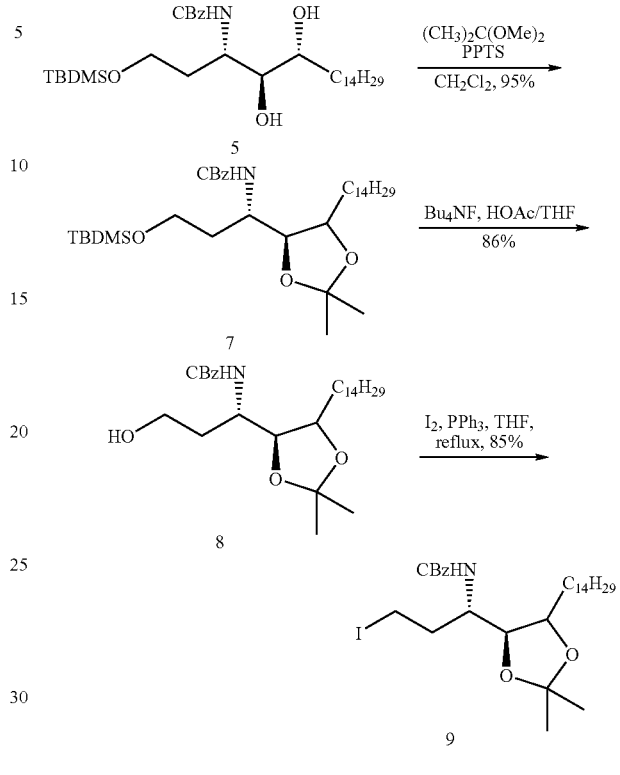

Dimethyl acetal (Johansson, R. et al., *J. Chem. Soc. PerkinTrans.* 1 1984, 2371-2374) and p-toluene sulfonic acid gave 4,6-O-(4-methoxybenzylidene)-β-D-1-thio-galactoside 12 in 86% yield. Benzylation of 12 followed by oxidation of thiogalactoside using MMPP gave sulfonyl galactoside 13 in good yield. N-benzlyation could not be avoided in this step.

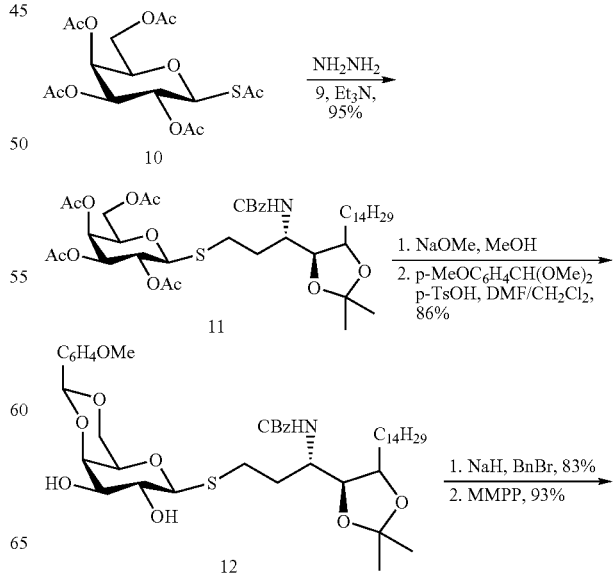

Acetonide formation was used to protect the 1,2-diols in compound 5 (Scheme 3), then the primary alcohol 8 was released by desilylation of 7. Because the basic fluoride ion caused the cyclization, acetic acid was added to Bu$_4$NF solution as the buffer (Niu, C. et al., *J. Org. Chem.* 1996, 61, 1014-1022) to afford 8 as the only product, since there was no cyclic compound formed. The iodo compound 9 can be made by one skilled in the art using PPh$_3$, iodine and imidazole reflux in THF (Spak, S. J. et al., *Tetrahedron* 2000, 56, 217-224).

Based on the general idea of synthesis of the model α-C-galactoside (Yang, G. et al., *Org. Lett.;* 1999, 1, 2149-2151), the synthesis was continued by treatment of thioacetate 10 with hydrazinium acetate in DMF under N$_2$ to deprotect thioacetate (Park, W. K. C. et al., *Carbohydr. Lett.* 1995, 1, 179-184). The freshly deprotected thio derivative was subsequently treated with electrophile 9 to provide thio-galactoside 11 in 95% overall yield (Scheme A4). Treatment of β-D-thio-galactoside 11 with NaOMe in MeOH followed by protection using p-methoxybenzaldehyde.

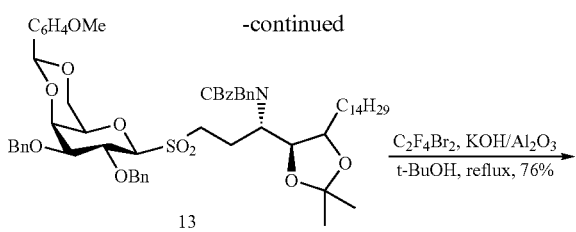

13

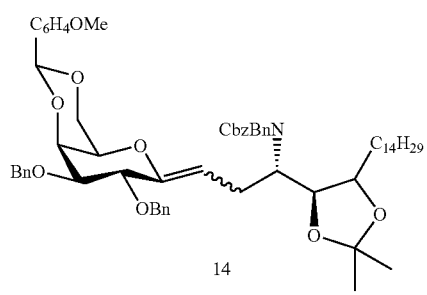

14

The RB reaction using $C_2F_4Br_2$/t-BuOH at reflux afforded the product 14 (Scheme A5). The ratio of Z:E alkene isomers was not determined because of peak broadening in the NMR. The intermediate 1-O-Methyl-2,3-dibenzyl β-galactoside can be made in one step by using chlorotrimethylsilane in methanol. Esterification of the primary hydroxyl group at C6 afforded the benzoate 15 in 88% yield (Scheme A5). Treatment of the acetonide 15 with 1N $HCl/Et_2O$ in methanol generated the corresponding diol 16. Cyclic carbonation of the diol using triphosgene (Burk, R. M. et al., *Tetrahedron Lett.* 1993, 34, 395-398) followed by silylation of the axial hydroxyl group at C4 afforded the silyl ether 17. Pump addition (McCombie, S. W. et al., *Tetrahedron Lett.* 1991, 32, 2083-2086) of 17 in $CH_2Cl_2$ (0.01M) to $BF_3 \cdot Et_2O$ in $CH_2Cl_2$ solution (4:1, 0.05M) afford α-C-galactoside 18 and cyclized compound 19 (20%). Treatment of silyl ether 18 with 1N $Bu_4NF$ in THF afforded product 20, which is identified by $^1H$ NMR (anomeric H: 3.95 ppm, $J_{12}$=4.6 Hz) and TLC.

Scheme A5

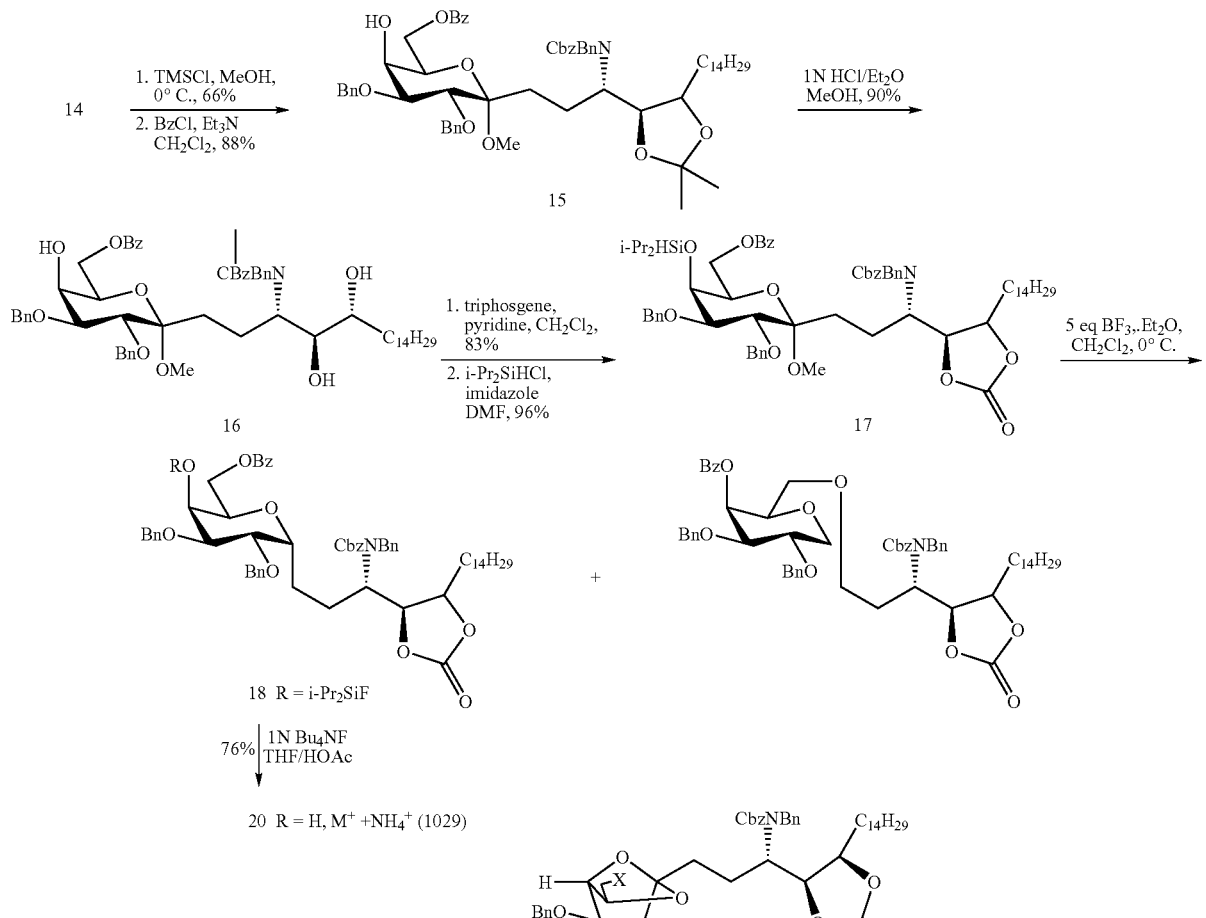

The carbonyl groups were removed prior to debenzylation. Compound 20 was treated with NaOH and refluxed in 1:1 dioxane and H₂O to afford the oxazolidinone 21 (Scheme A6). Hydrolysis of 21 gave the N-benzylamine 22, which was fully debenzylated by transfer hydrogenolysis (10% Pd/C, cyclohexene) (Roush, W. R. et al., *J. Org. Chem.* 1985, 50, 3752-3757) to afford crude 23 in 80% overall yield. The fatty

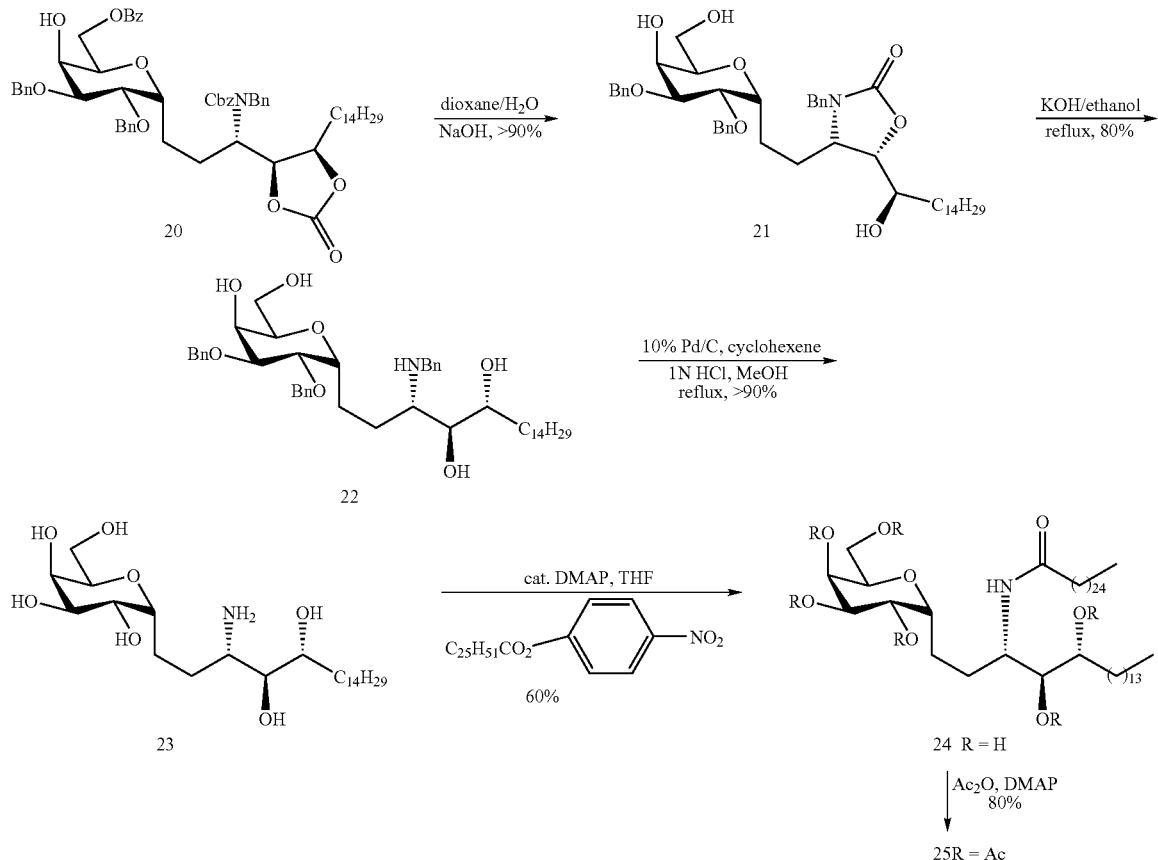

Scheme A6 amide chain was then introduced using p-nitrophenyl hexadeconate as the acylating agent to afford the target 24 (Morita, M. et al., *J. Med. Chem.* 1995, 38, 2176-2187). Final purification was done by flash chromatography on silica gel eluting with CHCl₃:MeOH (4:1). The $^1$H and $^{13}$C NMR and optical rotation {[α]$^{25}_D$ +40.8° (c=1.3, pyridine)}, mp 175-178° C., high resolution FABMS m/z 856.7601 (C₅₁H₁₀₁O₈N+H⁺ requires 856.7605) obtained for a sample of 24. The mass spectrum and $^1$H NMR of fully acylated compound 25 further confirmed that 24 was the right compound, namely, CRONY-101.

L-2-[(benzyloxycarbonyl)amino]-4-hydroxybutyric acid (1)

To a solution of L-homoserine 1 (4.0 g, 33.6 mmol) in 160 ml of 1N NaHCO₃ was added 6.0 ml (37 mmol) of benzyl chloroformate. The reaction mixture was stirred at 23° C. for 24 h and then extracted with ether (2×200 ml). The aqueous phase was ice cooled, carefully acidified to pH 2-3 with 3N HCl, and extracted with ethyl acetate (4×100 ml). The extract was dried over Na₂SO₄, filtered, and evaporated to afford 6.52 g (77%) product as a white solid. $^1$H NMR (Me₂CO-d₆, 300 MHz) δ 7.39-7.31(m, 1H, C₆H₅), 6.63 (d, J=7.7 Hz, 1H, NH), 5.08(s, 2H, CH₂Ph), 4.42(m, 1H, CH), 3.70(m, 2H, CH₂O), 2.05(m, 1H), 1.91(m, 1H).

Methyl-L-2-[(benzyloxycarbonyl)amino]-4-hydroxy-butyrate (2)

To a solution of above compound (5.7 g, 22.5 mmol) in 50 ml MeOH was added dropwise 2M trimethylsilyldiazomethane in hexanes (22.5 ml, 25 mmol) at 0° C. The reaction mixture was stirred at rt overnight. Basic dowex resin was added, filtered and rinsed by methanol. After evaporation of the methanol in room temperature, the residue was purified by flash chromatography on florisil eluting with 50% PE/EtOAc to afford 4.6 g (77%) 2 as a colorless oil. $^1$H NMR (CDCl₃, 300 MHz): δ 7.35 (s, 5H, C₆H₅), 5.69(d, J=6.6 Hz, 1H, NH), 5.12(s, 2H, CH₂Ph), 4.55(m, 1H), 3.76(s, 3H, OMe), 3.70(m, 2H), 2.81(br, 1H, OH), 2.15(m, 1H), 1.71(m, 1H). $^{13}$C NMR(CDCl$_3$, 75 MHz): δ 174.09, 153.72.136.21, 128.21, 128.61, 128.18, 67.42, 58.60, 52.77, 51.69, 35.33.

Methyl-L-2-[(benzyloxycarbonyl)amino]-4-O-(tert-butyldimethylsilyl)-butyrate

To a solution of 2 (4.19 g, 15.66 mmol) in 20 ml CH$_2$Cl$_2$ was added TBDMSCl (2.83 g, 18.8 mmol) followed by imidazole (2.55 g, 37.6 mmol). This reaction mixture was stirred at room temperature for 2 h. The mixture was filtered, rinsed by CH$_2$Cl$_2$ and washed with water. The solution was concentrated and purified by column chromatography on silica gel eluting with EtOAc-PE (30%) to afford 5.429 g (90%) product as a colorless oil. $^1$H NMR (CDCl$_3$, 300 MHz): δ 7.34(s, 5H, C$_6$H$_5$), 5.93(d, J=7.7 Hz, 1H, NH), 5.10(m, 2H, CH$_2$Ph), 4.45(m, 1H), 3.73(s, 3H, OMe), 3.68 (m, 2H), 2.00(m, 2H), 0.87(s, 9H), 0.04(s, 6H). $^{13}$C NMR (CDCl$_3$, 75 MHz): δ 172.72, 156.06, 136.35, 128.56, 128.12, 128.02, 66.99, 60.16, 52.88, 52.47, 34.13, 26.12, 18.46, −5.26.

L-2-[(benzyloxycarbonyl)amino]-4-O-(tert-butyldimethylsilyl)-butylaldehyde (3)

To a solution of above compound (5.42 g, 15.66 mmol) in 20 ml THF at −78° C. was added 1M DIBAL in heptane (43 ml, 42 mmol). The reaction mixture was stirred at −78° C. for 3 h. The resulting emulsion was slowly poured into 100 ml of ice-cold 1N HCl with stirring over 10 min, and the aqueous mixture was extracted with EtOAc (3×100 ml), dried over Na$_2$SO$_4$, filtered and concentrated in vacuo. The residue was purified by column chromatography on silica gel eluting with EtOAc-PE (20%) to afford 4.03 g (85%) 3 as a colorless oil. $^1$H NMR (CDCl$_3$, 300 MHz): δ 9.59 (s, 1H, CHO), 7.35(m, 5H, C$_6$H$_5$), 5.86(br, 1H, NH), 5.12(s, 2H, CH$_2$Ph), 4.30(m, 1H), 3.69(t, 2H), 2.14(m, 2H), 0.86(s, 9H), 0.03(s, 3H), 0.02(s, 3H). $^{13}$C NMR(CDCl$_3$, 75 MHz), δ 199.01, 156.18, 136.41, 128.65, 128.29, 128.16, 67.20, 59.21, 59.13, 32.16, 26.09, 18.42, −5.21, −5.30.

Preparation of Z-olefin (4)

To a suspension of pentadecylphosphonium bromide (5.52 g, 9.8 mmol; prepared from 1-bromopentadecane and triphenylphosphine, refluxed in toluene for 5 days, 98%) in THF (20 ml) was added dropwise NaHMDS (0.6M in toluene, 15 ml, 9.2 mmol) at −75° C. under nitrogen atmosphere. The solution was gradually warmed to 0° C. and stirred for 1 h. To this solution, which was cooled down to −75° C. again, aldehyde 3 (2.472 g, 7 mmol) in 8 ml THF was added dropwise over 30 min. After the reaction mixture was stirred at rt for 2 h, the reaction was quenched by addition of saturated NH$_4$Cl (100 ml) and extracted with ether. The organic extract was washed with brine, dried over Na$_2$SO$_4$, filtered and concentrated in vacuo. The residue was purified by column chromatography on silica gel eluting with EtOAc-PE (10%) to afford 3.44 g (85%) Z-olefin 4 as a colorless oil. $^1$H NMR (CDCl$_3$, 500 MHz): δ 7.34-7.31(m, 5H, C$_6$H$_5$), 5.47(after decoupling, d, J=10 Hz, 1H, vinyl H next to CH$_2$), 5.42(m, 1H, NH), 5.27(t, J=9.8 Hz, 1H, vinyl H next to CH), 5.09(m, 2H, CH$_2$Ph), 4.58(m, 1H), 3.67(m, 2H), 2.11(m, 2H), 1.73(m, 2H), 1.25(s, 22H), 0.89(s, 12H), 0.05(s, 3H), 0.04(s, 3H). $^{13}$C NMR(CDCl$_3$, 75 MHz): δ 155.71, 136.96, 132.39, 129.96, 128.52, 128.16, 128.02, 66.59, 60.34, 60.31, 47.24, 38.06, 32.21, 29.99, 29.85, 29.69, 29.65, 29.55, 29.50, 27.96, 26.17, 22.99, 18.43, 14.42, −5.15.

Dihydroxylation of olefin (Z)-4 using AD-mix-β

To a solution of AD-mix-β (6.294 g) and methanesulfonamide (0.427 g, 4.50 mmol) in t-BuOH/H$_2$O (1:1, 10 ml) was added Z-4 (2.45 g, 4.49 mmol) at 0° C. under nitrogen atmosphere. The mixture was stirred at rt for 48 h, quenched with Na$_2$S$_2$O$_3$ (6.7 g) and extracted with EtOAc. The organic extract was washed with 1N KOH, H$_2$O, brine and dried over Na$_2$SO$_4$. After evaporation of the solvent under the reduced pressure, the diols were purified by column chromatography (EtOAc/PE=30%) to give 6 (3,4 syn form, 0.5 g, 19% yield) and 5 (3,4-anti form, 1.7 g, 65% yield) as a white solid.

(3S,4R,5S)-1-O-(tert-butyldimethylsilyl)-3-[(benzyloxycarbonyl)amino-4,5-nonadecanediol (6)

mp 39-40° C. [α]$^{25}$ 3.0° (c 9, CHCl$_3$). $^1$H NMR (CDCl$_3$, 300 MHz): δ 6.36(s, 5H, C$_6$H$_5$), 5.29(d, J=8.8 Hz, 1H, NH), 5.01(s, 2H, CH$_2$Ph), 4.16(m, 1H), 3.73(t, J=5.6 Hz, 2H), 3.59(br, 1H), 3.34(m, 2H), 3.04(d, J=4.0 Hz, 1H), 1.86(m, 2H), 1.73(m, 1H), 1.55(m, 1H), 1.26(s, 24H), 0.89(s, 12H), 0.06(s, 6H). $^{13}$C NMR(CDCl$_3$, 75 MHz): δ 157.64, 136.38, 128.68, 128.35, 128.22, 76.43, 71.53, 67.38, 60.08, 50.22, 49.86, 35.46, 33.52, 32.23, 30.10, 30.00, 29.96, 29.66, 26.11, 23.00, 18.43, 14.43, −5.20, −5.23.

(3S,4S,5R)-1-O-(tert-butyldimethylsilyl)-3-[(benzyloxycarbonyl)amino-4,5-nonadecanediol (5)

mp 40-43° C. [α]$^{25}$ 16.3° (c 9, CHCl$_3$). $^1$H NMR (CDCl$_3$, 300 MHz): δ 7.38(s, 5H, C$_6$H$_5$), 5.61(d, J=8.0 Hz, 1H, NH), 5.08(s, 2H, CH$_2$Ph), 4.09(m, 1H), 3.73(m, 3H), 3.57(m. 1H), 3.49(m, 1H), 2.11(br, 1H), 1.95-1.76(m, 12H), 1.26(s, 26H), 0.89(s, 12H), 0.07(s, 6H). $^{13}$C NMR(CDCl$_3$, 75 MHz): δ 156.41, 136.57, 128.58, 128.17, 128.12, 76.26, 73.22, 66.95, 59.98, 51.36, 33.77, 32.19, 32.05, 29.63, 26.12, 26.04, 22.96, 18.44, −5.20, −5.27.

(3S,4S,5R)-1-O-(tert-butyldimethylsilyl)-3-[(benzyloxycarbonyl)amino-4,5-O-isopropylidene-nonadecane (7)

To a solution of diol 5 (2.23 g, 3.85 mmol) in 30 ml CH$_2$Cl$_2$ was added 2,2-dimethoxy propane (2.37 ml, 19.3 mmol) followed by PPTs (97 mg, 0.38 mmol). After the reaction mixture was stirred at rt for 1.5 h, 50 ml saturated NaHCO$_3$ was added and extracted with CH$_2$Cl$_2$ (30 ml×2). The organic phase was dried over Na$_2$SO$_4$. After evaporation of the solvent under the reduced pressure, the residue was purified by column chromatography (EtOAc/PE=10%) to give product 7 (2.287 g, 96% yield) as an oil. $^1$H NMR (CDCl$_3$, 300 MHz): δ 7.34(s, 5H, C$_6$H$_5$), 5.17(d, J=8.8 Hz, 1H, NH), 5.07(s, 2H, CH$_2$Ph), 4.13(m, 2H), 3.90(m, 1H), 3.78-3.70(m, 2H), 1.89(m, 2H), 1.56(m, 2H), 1.43(s, 3H), 1.33(s, 3H), 1.25(s, 24H), 0.88(s, 12H), 0.04(s, 3H), 0.03(s, 3H). $^{13}$C NMR(CDCl$_3$, 75 MHz): δ 155.86, 136.77, 128.47, 128.02, 107.78, 79.39, 77.96, 66.68, 60.25, 49.19, 34.40, 32.16, 29.92, 29.59, 29.12, 27.44, 27.01, 26.13, 25.61, 22.92, 18.39, 14.35, −5.25, −5.28.

(3S,4S,5R)-3-[(benzyloxycarbonyl)amino-4,5-O-isopropylidene-nonadecanol (8)

To a solution of above compound (3.31 g, 5.33 mmol) in 25 ml THF was added 1M Bu$_4$NF in THF (12 ml) followed by 0.5 ml acetic acid. After the reaction mixture was stirred at rt overnight, 20 ml saturated NaHCO$_3$ was added and extracted with CH$_2$Cl$_2$ (50 ml×2). The organic phase was dried over Na$_2$SO$_4$. After evaporation of the solvent under the reduced pressure, the residue was purified by column chromatography (EtOAc/PE=50%) to give 8 (2.56 g, 90% yield) as a white solid. Mp 58-60° C. [α]$^{25}$ –3.67° (c 3, CHCl$_3$). $^1$H NMR (CDCl$_3$, 300 MHz): δ 7.36(s, 5H, C$_6$H$_5$), 5.11(s, 2H, CH$_2$Ph), 4.86(br, 1H, NH), 4.12(m, 1H), 4.03-3.92(m, 2H), 3.72(m, 2H), 2.82(br, 1H, OH), 2.02(m, 2H), 1.52(m, 24H), 1.44(s, 3H), 1.33(s, 3H), 0.88(t, J=6.6 Hz, 3H). $^{13}$C NMR(CDCl$_3$, 75 MHz): δ 156.91, 136.38, 128.72, 128.41, 128.22, 108.28, 79.78, 78.03, 77.44, 77.39, 77.02, 67.38, 59.06, 48.70, 35.36, 32.21, 30.16, 29.99, 29.90, 29.85, 29.65, 29.25, 27.04, 25.74, 22.98, 14.42.

(3S,4S,5R)-1-iodo-3-[(benzyloxycarbonyl)amino-4,5-O-isopropylidene-nonadecane (9)

A mixture of 8 (2.5 g, 4.95 mmol), PPh$_3$ (1.63 g, 6.1 mmol), imidazole (0.87 g, 11.8 mmol) and iodine (2.03 g, 7.4 mmol) in THF (50 ml) was stirred under reflux for 2.5 h. After evaporation of the solvent, the crude product was dissolved in CH$_2$Cl$_2$ (100 ml) and solids were removed by filtration. An equal volume of saturated aqueous NaHCO$_3$ was added and the mixture was stirred for 10 min. Iodine was added in portions and when the organic phase remained iodine-colored, the mixture was stirred for an additional 10 min. Excess iodine was destroyed by the addition of saturated aqueous Na$_2$S$_2$O$_3$ solution. The organic layer was diluted with CH$_2$Cl$_2$ (50 ml), separated, washed with water (50 ml), dried over Na$_2$SO$_4$. After evaporation of the solvent under the reduced pressure, the residue was purified by column chromatography (EtOAc/PE=20%) to give 9 (2.57 g, 87% yield) as a white solid. Mp 79-81° C. $^1$H NMR (CDCl$_3$, 300 MHz): δ 7.33(s, 5H, C$_6$H$_5$), 5.07(m, 34.05(m, 3H), 3.78(m, 1H), 3.23(m, 2H), 2.26(m, 2H), 1.89(m, 2H), 1.42(s, 3H), 1.30(s, 3H), 1.55-1.26(m, 24H), 0.88(t, J=6.6 Hz, 3H). $^{13}$C NMR(CDCl$_3$, 75 MHz): δ 155.88, 136.35, 128.59, 128.26, 128.21, 108.11, 79.57, 77.75, 67.11, 52.56, 36.72, 32.14, 30.35, 30.26, 29.91, 29.81, 29.76, 29.58, 29.15, 27.36, 26.99, 25.51, 22.91, 14.37.

(3'S,4'S,5'R)3'-[(benzyloxycarbonyl)amino-4',5'-O-isopropylidene-nonadecanylthio]2,3,4,6-tetra-O-acetyl-β-D-galactopyranose (11)

To a degassed solution of 2.02 g (4.98 mmol) β-2,3,4,6-tetra-O-acetyl-galactosyl thioacetate 10 in 15 ml DMF, NH$_2$NH$_2$.HOAc (0.47 g, 5.96 mmol) was added. This solution was degassed at room temperature for 1 h. Iodide 9 (2.55 g, 4.14 mmol) was added, followed by triethyl amine (0.64 ml, 6.58 mmol). After 2 h, 100 ml ethyl acetate and 50 ml water were added. The organic layer was washed with water and brine, and dried over anhydrous sodium sulfate. After evaporation of the organic solvent, the residue was purified by chromatography on silica gel eluting with 50% EtOAc/PE to afford 3.2 g β-thiogalactoside 11 (90% yield) as a sticky oil. $^1$H NMR (300 MHz, CDCl$_3$): δ 7.32 (s, 5H), 5.42 (d, J=3.0 Hz, 1H, H-4), 5.24(t, J=9.9 Hz, 1H, H-2), 5.10(m, 2H), 5.03(dd, J=3.3, 9.9 Hz, 1H, H-3), 4.83(d, J=9.5 Hz, 1H, NH), 4.46(d, J=9.9 Hz, 1H, H-1), 4.13(m, 3H), 4.04(t, J=5.8 Hz, 1H, H-5), 3.94(t, 1H), 3.79(m, 1H), 2.85-2.72(m, 2H, H—SCH$_2$), 2.12(s, 3H, H—OAc), 2.05(s, 3H, H—OAc), 2.04(s, 3H, H—OAc), 1.98(s, 3H, H—OAc), 1.76(m, 1H), 1.54(m, 1H), 1.43(s, 3H), 1.32(s, 3H), 1.26(s, 24H), 0.88(t, J=6.6 Hz, 3H). $^{13}$C NMR (75 MHz, CDCl$_3$): δ 170.27, 170.21, 170.04 169.56, 155.77, 136.49, 128.60, 128.24, 128.12, 108.09, 84.30, 77.77, 77.45, 77.05, 76.96, 74.62, 72.05, 67.38, 67.32, 66.99, 61.43, 50.97, 32.44, 32.14, 30.26, 30.18, 29.92, 29.82, 29.28, 27.55, 26.95, 26.78, 26.75, 25.64, 22.91, 21.02, 20.87, 20.84, 14.35.

(3'S,4'S,5'R)3'-[(benzyloxycarbonyl)amino-4',5'-O-isopropylidene-nonadecanylthio]4,6-O-benzylidene-β-D-galactopyranose (12)

Into the solution of 2.31 g (2.71 mmol) of 2,3,4,6-tetra-O-acetyl-β-thio-galactoside 11 and 50 ml methanol was added NaOMe (70 mg, 1.3 mmol). The mixture was stirred at rt until a white precipitate was formed. The precipitate was dissolved in EtOAc, then acidic resin was added until the pH of the solution was neutral. The resin was filtered off and rinsed by EtOAc. The solution was concentrated until completely dry to afford 1.76 g of a white solid. To a mixture of above solid (1.75 g, 2.57 mmol), p-methoxybenzaldehyde dimethyl acetal (1.1 ml, 6.42 mmol), and 50 ml dry CH$_2$Cl$_2$ and 3 ml DMF was added p-toluene sulfonic acid monohydrate (29 mg) at room temperature. After 2 h, the mixture was neutralized with triethyl amine (1 ml) and concentrated. The residue was chromatographed (SiO$_2$, EtOAc/MeOH, 100% to 95%) to give 12 (1.72 g, 86% overall yield) as a white solid. $^1$H NMR (300 MHz, CDCl$_3$): δ 7.48(d, J=8.8 Hz, 2H), 7.29(m, 5H), 6.82(d, J=8.8 Hz, 2H), 5.43(s, 1H), 5.06(m, 3H), 4.17(d, 2H), 4.16(s, 1H), 4.05(m, 1H), 3.90(m, 3H), 3.75(s, 3H), 3.61(m, 2H), 3.39(s, 1H), 2.89(m, 1H), 2.68(m, 1H), 2.05(m, 2H), 1.80(m, 2H), 1.60-1.20(m, 30H), 0.88(t, 3H). $^{13}$C NMR (75 MHz, CDCl$_3$): δ 160.14, 156.19, 136.45, 130.37, 128.56, 128.16, 128.08, 127.75, 113.61, 108.03, 101.17, 85.69, 79.64, 77.76, 75.74, 73.88, 70.19, 69.33, 68.98, 67.00, 55.38, 50.59, 32.62, 32.09, 29.88, 29.79, 29.73, 29.53, 29.11, 27.50, 26.95, 25.63, 25.33, 22.87, 14.33.

(3'S,4'S,5'R)3'-[(benzyloxycarbonyl)benzylamino-4',5'-O-isopropylidene-nonadecanylthio]4,6-O-benzylidene-2,3-di-O-benzyl-β-D-galactopyranose β-S-galactoside 12 (1.49 g, 1.86 mmol) was dissolved in 20 ml THF and 5 ml DMF, NaH (0.6 g, 60% in mineral oil) was added, the mixture was stirred at rt for ½ h, then 0.068 g (0.186 mmol) tetra-butylammonium iodide was added followed by 0.89 ml benzyl bromide (7.44 mmol). After the mixture was stirred at room temperature overnight, the reaction was quenched with 10 ml of MeOH. The resulting solution was added to 50 ml H$_2$O and extracted by EtOAc (100 ml×3). The organic phase was washed by brine, and dried over Na$_2$SO$_4$ and concentrated. The residue was chromatographed on a column of silica gel (eluted with 30% EtOAc-petroleum ether) to afford 1.62 g product (83%) as a colorless oil. MS: m/z 1094(M$^+$+Na$^+$), (calcd. C$_{65}$H$_{85}$O$_{10}$SN, 1071). $^1$H NMR (300 MHz, CDCl$_3$): δ 7.48(d, J=8.8 Hz, 2H), 7.43-7.22(m, 20H), 6.88(d, J=8.8 Hz, 2H), 5.46(s, 1H), 5.17(m, 2H), 4.78(m, 6H), 4.34(m, 4H), 4.16(d, J=3.3 Hz, 1H), 4.14(m, 1H), 3.95(m, 1H), 3.79(s, 3H), 3.59(dd, J=3.3, 9.1 Hz, 1H), 3.50(m, 1H), 3.29(m, 1H), 2.70(m, 2H), 2.06(m, 2H), 1.47-1.13(m, 32H), 0.92(t, 3H). $^{13}$C NMR (75 MHz, CDCl$_3$): δ 160.06, 158.66, 139.19, 138.55, 138.41, 136.43, 130.64, 128.41, 128.33, 128.09, 127.84, 127.78, 127.67, 127.50, 127.34, 127.31, 127.21, 127.08, 113.57, 107.69, 101.33, 81.23, 79.64, 79.59, 79.42, 77.88, 75.79, 73.99, 71.77, 69.99, 69.40, 55.41, 32.14, 30.99, 30.08, 29.92, 29.85, 29.63, 29.57, 27.74, 25.54, 22.91, 14.35.

(3'S,4'S,5'R)3'-[(benzyloxycarbonyl)benzylamino-4', 5'-O-isopropylidene-nonadecanylsulfonyl]4,6-O-benzylidene-2,3-di-O-benzyl-β-D-galactopyranose (13)

A solution of MMPA (2.1 g, 4.26 mmol) in $H_2O$ (10 ml) was added to a solution of thio-galactoside (1.52 g, 1.42 mmol) in EtOH (10 ml) and THF (10 ml), the mixture was kept at 60° C. for 3 h. The mixture was concentrated in vacuo to dryness. The residue was treated with 50 ml saturated $NaHCO_3$ solution, and extracted with EtOAc (50 ml×3), dried over $Na_2SO_4$ and evaporated to dryness. The residue was purified by chromatography on silica gel eluting with 40% EtOAc/PE to afford pure sulfone 13 (1.45 g, 93%) as a white solid. mp. 40-43° C. MS: m/z 1121($M^+$+$NH_4^+$), (calcd. $C_{65}H_{85}O_{12}SN$, 1103). $^1H$ NMR ($CDCl_3$, 400 MHz heated at 55° C.): δ 7.46-7.18(m, 22H), 6.88(d, J=8.8 Hz, 2H), 5.39(s, 1H), 5.13(s, 2H), 4.95(d, 1H), 4.84(d, 1H), 4.73(s, 2H), 4.65(m, 1H), 4.42(t, J=9.6 Hz, 1H), 4.30(m, 2H), 4.24(s, 1H), 4.22(d, 2H), 4.11(d, 1H), 4.07(m, 1H), 3.91(dd, 1H), 3.79(s, 3H), 3.66(dd, 1H), 3.55(b, 1H), 3.32(s, 1H), 3.28(b, 1H), 3.00(b, 1H), 2.35(m, 1H), 2.20(b, 1H), 1.34(s, 3H), 1.25(s, 28H), 1.17(s, 3H), 0.89(t, 3H). $^{13}C$ NMR (75 MHz, $CDCl_3$): δ 160.39, 156.97, 138.64, 138.07, 136.21, 130.39, 128.81, 128.68, 128.60, 128.43, 128.06, 127.90, 127.72, 127.59, 113.86, 107.98, 101.59, 80.80, 78.93, 77.93, 77.42, 76.58, 75.78, 73.27, 73.11, 72.10, 70.71, 68.92, 55.56, 32.21, 30.00, 29.96, 29.92, 29.65, 28.03, 26.36, 25.67, 22.98, 14.41.

(3'S,4'S,5'R)3'-[(benzyloxycarbonyl)benzylamino-4', 5'-O-isopropylidene]4,6-O-benzylidene-2,3-di-O-benzyl-β-D-galactopyranosylidene Nonadecane (14)

To a solution of 1.45 g 13 (1.32 mmol) in 10 ml t-BuOH and 10 ml $CF_2BrCF_2Br$, 4 g 25% (by weight) $KOH/Al_2O_3$ (prepared one day earlier) was added. This mixture was refluxed at 47° C. for 10 h. The solution was filtered through a pad of celite which was washed by $CH_2Cl_2$. The residue was purified by column chromatography on silica gel eluting with 25% EtOAc-PE to afford 0.6 g 14 (60% based on recovered starting material) as a colorless oil. MS: m/z 1060($M^+$+$Na^+$), (calcd. $C_{65}H_{83}O_{10}N$, 1037). $^1H$ NMR (300 MHz, $CDCl_3$), δ 7.46 (d, J=8.8 Hz, 2H), 7.39-7.10(m, 20H), 6.87(d, J=8.8 Hz, 2H), 5.50(s, 1H), 5.40(t, 1H), 5.13(m, 2H), 4.97(d, 1H), 4.82-4.66(m, 5H), 4.52(m, 1H), 4.40-4.24(m, 3H), 4.09-3.99(m, 2H), 3.79(s, 3H), 3.72(m, 1H), 3.58(m, 1H), 3.48(m, 1H), 2.54(t, 2H), 1.41-1.12(m, 32H), 0.89(t, 3H).

Benzoate (15)

To a solution of 0.6 g 14 (Z+E, 0.578 mmol) in 10 ml MeOH, TMSCl (73 μl) was added at 0° C. After the mixture was stirred at 0° C. for 30 min, 20 ml saturated $NaHCO_3$ was added. The mixture was extracted with $CH_2Cl_2$ (2×40 ml). The organic phase was dried over $Na_2SO_4$, concentrated, the residue was purified by column chromatography on silica gel eluting with 35% EtOAc-PE to afford 0.36 g product (66%). $^1H$ NMR (300 MHz, $CDCl_3$): δ 7.28(m, 20H), 5.08(m, 2H), 4.90(d, 1H), 4.68(s, 2H), 4.61(d, 1H), 4.56(d, 1H), 4.51(d, 1H), 4.35(d, 1H), 4.02-3.95(m, 4H), 3.84-3.81(m, 3H), 3.65(m, 1H), 3.58(m, 1H), 3.00(s, 3H), 2.59(br, 1H), 2.23(br, 1H), 1.51(m, 4H), 1.39(s, 3H), 1.33(s, 26H), 1.20(s, 3H), 0.89(t, 3H).

To a solution of above compound 0.36 g (0.378 mmol) in 10 ml $CH_2Cl_2$, BzCl (66 μl, 0.56 mmol) was added at 0° C., followed by $Et_3N$ (0.3 ml, 2.3 mmol). After the mixture was stirred at 0° C. for 2 h, 20 ml 10% ammonia solution was added. The mixture was extracted with $CH_2Cl_2$ (2×40 ml). The organic phase was dried over $Na_2SO_4$, concentrated, the residue was purified by column chromatography on silica gel eluting with 25% EtOAc-PE to afford 0.365 g product 15 (92%).

To a solution of 0.365 g 15 (0.347 mmol) in 10 ml MeOH, 1N $HCl/Et_2O$ (1 ml) was added at 0° C. After the mixture was stirred at 0° C. for 2 h, 20 ml saturated $NaHCO_3$ was added. The mixture was extracted with $CH_2Cl_2$ (2×40 ml). The organic phase was dried over $Na_2SO_4$, and concentrated, the residue was purified by column chromatography on silica gel eluting with 30% EtOAc-PE to afford 0.275 g product 16 (80%). $^1H$ NMR (300 MHz, $CDCl_3$): δ 7.92(d, J=7.3 Hz, 2H), 7.53(t, 1H), 7.39-7.20(22H), 5.15(d, 1H), 4.94(m, 2H), 4.74-4.69(m, 3H), 4.63(br, 1H), 4.55(m, 2H), 4.43(br, 1H), 4.08-3.93(m 5H), 3.55(d, 1H), 3.42(m, 1H), 3.11(s, 3H), 2.17(br, 1H), 1.76(m, 2H), 1.47(m, 2H), 1.25(s, 26H), 0.89(t, 3H). $^{13}C$ NMR (75 MHz, $CDCl_3$): δ 166.35, 157.80, 138.54, 136.34, 133.09, 130.21, 129.82, 129.71, 128.66, 128.60, 128.48, 128.43, 128.22, 128.04, 127.96, 127.79, 127.60, 103.18, 79.89, 79.05, 75.91, 75.58, 73.17, 72.60, 69.34, 68.17, 67.83, 64.57, 47.81, 33.80, 33.78, 32.18, 29.96, 29.60, 27.81, 25.89, 22.93, 14.30.

Cyclic Carbonate

To a solution of 0.27 g 16 (0.266 mmol) in 4 ml $CH_2Cl_2$ and pyridine 0.13 ml, 40 mg (0.133 mmol) triphosgene in 1 ml $CH_2Cl_2$ was dropwide added at −70° C. After the addition was finished, the reaction mixture was warmed up to room temperature. After 1.5 h, the mixture was diluted with $CH_2Cl_2$ (30 ml), quenched with 20 ml saturated $NH_4Cl$, then extracted with $CH_2Cl_2$ (20 ml×30). The organic phase was washed with 1N HCl, saturated $NaHCO_3$, and brine. The organic layer was dried over $Na_2SO_4$, concentrated, the residue was purified by column chromatography on silica gel eluting with 20% EtOAc-PE to afford 0.265 g product (90%). $^1H$ NMR (300 MHz, $CDCl_3$): δ 8.06(d, J=7.3 Hz, 2H), 7.58(t, 1H), 7.46(t, 2H), 7.36-7.24(m, 19H), 7.05(m, 1H), 5.16(m, 2H), 4.99(d, 1H), 4.71-4.49(m, 8H), 4.32(m, 1H), 4.09(m, 1H), 4.03(dd, 1H), 3.90(m, 1H), 3.82(m, 2H), 3.14-3.05(two singlets, 3H), 2.48(s, 1H), 1.85(m, 1H), 1.66 (m, 3H), 1.46(m, 2H), 1.27(s, 24H), 0.89(t, 3H). $^{13}C$ NMR (75 MHz, $CDCl_3$): δ 166.41, 156.85, 153.62, 138.54, 138.47, 138.34, 138.32, 138.04, 136.19, 133.13, 129.82, 128.87, 128.72, 128.56, 128.35, 128.25, 128.13, 128.08, 127.97, 127.84, 127.75, 127.61, 127.57, 127.52, 101.95, 80.64, 79.96, 79.85, 77.48, 77.42, 77.11, 77.02, 76.90, 75.41, 72.53, 69.30, 68.24, 67.69, 64.35, 55.47, 48.21, 32.28, 32.20, 29.97, 29.79, 29.73, 29.61, 29.19, 28.92, 28.47, 25.66, 22.93, 14.30.

Silyl Ether (17)

To a solution of 260 mg above material (0.249 mmol) in 5 ml DMF, i-$Pr_2SiHCl$ 0.13 ml (0.75 mmol) and 101 mg imidazole were added. After the mixture was stirred at rt for 2 h, the solution was concentrated and purified by column chromatography on silica gel eluting with 30% EtOAc-PE to afford 0.228 g 17 (87%) as a colorless oil. MS: m/z 1173 ($M^++NH_4^+$), (calcd. $C_{69}H_{93}O_{12}SiN$, 1155). $^1H$ NMR (300 MHz, $CDCl_3$), δ 8.06(d, 7.3 Hz, 2H), 7.59(t, 1H), 7.47(t, 2H), 7.40-7.29(m, 19H), 7.04(m, 1H), 5.15(m, 2H), 5.01(d, 1H), 4.80(d, 1H), 4.65(m, 2H), 4.54-4.32(m, 7H), 3.99(m, 2H), 3.89(m, 1H), 3.80(m, 2H), 3.16-3.06(two singlets, 3H), 1.92(m, 1H), 1.69(m, 1H), 1.47(m, 2H), 1.27(s, 26H), 1.07 (m, 14H), 0.89(t, 3H). $^{13}C$ NMR (75 MHz, $CDCl_3$): δ 166.35, 156.88, 153.54, 138.68, 138.32, 133.15, 132.36, 130.36, 129.79, 128.91, 128.57, 127.47, 128.39, 128.22, 128.08, 127.90, 127.77, 127.70, 127.57, 127.51, 127.44, 127.40, 127.35, 101.95, 80.71, 80.29, 79.68, 77.43, 77.38, 77.11, 77.02, 76.98, 75.56, 73.16, 71.56, 70.55, 68.28, 64.55, 48.13, 32.21, 29.97, 29.93, 29.79, 29.71, 29.62, 29.26, 28.97, 25.57, 22.94, 17.95, 17.91, 17.84, 17.77, 14.31, 13.22, 13.16.

α-C-glycoside (20)

Syringe pump addition of a solution (92 mg, 0.079 mmol 17 in 6 ml $CH_2Cl_2$) to a solution of $BF_3.Et_2O$ (50 μl, 0.4 mmol) in 6 ml $CH_2Cl_2$ was carried out over a 5 h reaction time. The mixture was then treated with 20 ml sat. $NaHCO_3$, and extracted with $CH_2Cl_2$ (20 ml×3). The organic solvent was concentrated to afford a mixture of 18 and 19.

To the above crude products in 5 ml THF and 30 μl acetic acid, 0.4 ml 1N $Bu_4NF$ was added. The reaction was stirred at rt for 1 h, the mixture was diluted with $CH_2Cl_2$, washed with water. The organic was dried over $Na_2SO_4$, concentrated, the residue was purified by column chromatography on silica gel eluting with 20% EtOAc-PE to afford 61 mg product 20 (76%) and 18 mg side product 19 (20%). MS: m/z 1029($M^++NH_4^+$), (calcd. $C_{66}H_{77}O_{11}N$, 1011). $^{13}C$ NMR (75 MHz, $CDCl_3$): δ 166.54, 156.86, 153.59, 138.48, 138.30, 138.12, 136.17, 133.10, 130.36, 129.84, 128.89, 128.71, 128.61, 128.49, 128.41, 128.27, 128.23, 128.12, 127.95, 127.85, 127.68, 80.54, 79.76, 77.76, 77.50, 77.43, 76.22, 73.67, 73.03, 72.94, 70.30, 68.32, 67.53, 63.83, 55.20, 32.18, 29.96, 29.78, 29.66, 29.60, 29.23, 28.92, 25.52, 23.06, 22.93, 14.30.

Oxazolidinone (21)

Carbonate 20 (66 mg, 0.065 mmol) was dissolved in 5 ml dioxane:$H_2O$ (1:1) and treated with NaOH 0.46 g and heated under reflux conditions at 90° C. overnight. The sample was concentrated in vacuo and redissolved in $CHCl_3$ and washed with saturated $NH_4Cl$ solution. The aqueous layer was extracted with $CHCl_3$ (20 ml×3). The organic was dried over $Na_2SO_4$, concentrated, the residue was dried in vacuo to afford 50 mg product 21 (96%). MS: m/z 774($M^++H^+$), (calcd. $C_{47}H_{67}O_8N$, 773). $^1H$ NMR (500 MHz, $CDCl_3$): δ 7.35-7.26(m, 15H), 4.84(d, J=15.0 Hz, 1H), 4.73(m, 2H), 4.67(d, J=10.0 Hz, 1H), 4.56(d, J=11.5 Hz, 1H), 4.21(t, J=8.5 Hz, 1H), 4.05(d, J=15.0 Hz, 1H), 3.96-3.87(m, 4H), 3.82(t, J=7.5 Hz, 1H), 3.66(d, J=10.0 Hz, 1H), 3.60(m, 1H), 3.54(dd, J=3.0, 8.5 Hz, 1H), 3.47(m, 1H), 2.53(br, 2H, OH), 2.36(br, 1H, OH), 1.98(m, 1H), 1.78(m, 1H), 1.69(m, 2H), 1.57(m, 2H), 1.42(m, 2H), 1.25(m, 22H), 0.88(t, J=6.5 Hz, 3H). $^{13}C$ NMR (75 MHz, $CDCl_3$): δ 157.97, 138.50, 138.06, 128.92, 128.67, 128.58, 128.16, 127.96, 127.85, 79.49, 78.14, 76.23, 74.51, 73.81, 72.76, 71.08, 68.91, 68.41, 63.28, 57.34, 46.80, 34.99, 32.17, 29.94, 29.59, 24.94, 24.45, 22.92, 22.13, 14.30.

Benzylamine (22)

The crude compound 21 (50 mg, 0.063 mmol) was dissolved in 5 ml EtOH and 1 ml $H_2O$ and treated with KOH (0.5 g) at reflux overnight. The cooled solution was diluted with saturated $NH_4Cl$ solution and extracted with EtOAc (20 ml×3). The organic extracts were dried over $Na_2SO_4$, filtered, and concentrated, the residue was purified by column chromatography on silica gel eluting with $CHCl_3$:MeOH (4:1) to afford 39 mg product 22 (80%). MS: m/z 478($M^++H^+$), (calcd. $C_{46}H_{69}O_7N$, 477). $^1H$ NMR (300 MHz, $CDCl_3$): δ 7.35-7.25(m, 15H), 4.76-4.70(m, 3H), 4.59(d, J=11.7 Hz, 1H), 3.97-3.85(m, 4H), 3.77(s, 2H), 3.69(dd, J=3.6, 12.1 Hz, 1H), 3.60(m, 3H), 3.52(m, 1H), 3.30(t, J=6.6 Hz, 1H), 2.79(br, 5H), 1.88(m, 1H), 1.73(m, 2H), 1.57(m, 2H), 1.25(s, 25H), 0.89(t, J=6.9 Hz, 3H). $^{13}C$ NMR (75 MHz, $CDCl_3$): δ 138.56, 138.19, 128.70, 128.58, 128.51, 128.17, 128.12, 127.95, 127.87, 127.43, 78.06, 76.48, 74.60, 74.42, 73.99, 73.84, 72.79, 71.34, 68.53, 68.50, 68.12, 67.70, 63.14, 60.97, 51.85, 34.66, 32.20, 30.18, 29.99, 29.63, 25.76, 25.69, 22.95, 21.91, 14.33.

3'S,4'S,5'R-3'-N-hexacosanoyl-4',5'-dihydroxynonadecyl-α-C-D-galactopyranoside (23)

A solution of benzylamine 22 (39 mg, 0.052 mmol) in 1 ml MeOH was treated with 10% Pd/C (40 mg), 1N HCl (52 μl, 0.052 mmol), and cylcohexene (0.2 ml). (Roush et al., *J. Org. Chem.* 1985 50, 3752-3757). The resulting slurry was heated at reflux for 4 h, then cooled to room temperature, filtered through a pad of celite and basic resin, and concentrated to give 23 mg of crude 23. A solution of this material in THF (1 ml) was treated with p-nitrophenyl hexacosanoate (75 mg, 0.144 mmol) (Morita et al., *J. Med. Chem.* 1995, 38 2176-2187) and a crystal of DMAP. The resulting solution was stirred at rt for 48 h and concentrated. The residue was purified by column chromatography on silica gel eluting with $CHCl_3$:MeOH (4:1) to afford 23 mg product 24 (60%) as a white solid. Mp: 175-178° C. $[α]^{25}$ 40.8° (c 1.3, pyridine). FABMS (high-res.): m/z (calcd. $C_{51}H_{101}O_8N+H^+$, 856.7605. found 856.7601). $^1H$ NMR (500 MHz, $C_5D_5N$): δ 8.47(d, J=8.8 Hz, 1H, NH), 6.78-6.00(br, 6H, OH), 5.14(m, 1H), 4.74(dd, J=5.5, 8.8 Hz, 1H), 4.52(m, 3H), 4.37(dd, J=4.3, 11.0 Hz, 1H), 4.25(m, 4H), 2.72(m, 1H), 2.59(m, 1H), 2.48(m, 3H), 2.33(m, 2H), 2.22(m, 1H), 1.94 (m, 2H), 1.86(m, 3H), 1.71(m, 1H), 1.37(s, 64H), 0.88(t, J=6.4 Hz, 6H). $^{13}C$ NMR (100 MHz, $C_5D_5N$): δ 173.36, 78.37, 76.90, 73.65, 72.53, 72.07, 70.46, 70.27, 62.61, 52.56, 36.86, 34.33, 32.00, 30.26, 30.07, 29.88, 29.70, 29.49, 26.42, 22.81, 14.15.

3'S,4'S,5'R-3'-N-hexacosanoyl-4',5'-di-O-acetylnonadecacyl-2,3,4,6-tetra-O-acetyl-α-C-D-galactopyranoside (25)

To a solution of 24 (6 mg, 5.86 μmol) in 1 ml EtOAc, $Ac_2O$ (15 μl, 0.158 mmol) and DMAP (1 mg, 8.19 μmol) were added. The mixture was stirred at rt overnight. The residue was purified by column chromatography on silica gel eluting with EtOAc:PE (40%) to afford 5 mg product 25 (80%). MS: m/z ($M^++H^+$), 1108, ($M^++Na^+$), 1130, (calcd. $C_{63}H_{113}O_{14}N$, 1107). $^1H$ NMR (500 MHz, $C_6D_6$): δ 5.56(m, 2H), 5.42(dd, J=3.0, 9.0 Hz, 1H), 5.27(d, J=9.0 Hz, 2H), 5.16(d, J=10.0 Hz, 1H), 4.46(m, 2H), 4.33(m, 1H), 4.10(dd, J=5.0, 11.5 Hz, 1H), 3.74(m, 1H), 2.01(m, 3H), 1.83(s, 3H), 1.81(s, 3H), 1.78(s, 3H), 1.73(s, 3H), 1.70(s, 3H), 1.62(s, 3H), 1.45(m, 1H), 1.35-1.31(m, 74H), 0.90(m, 6H).

2. Synthesis of CRONY 101 by Method B

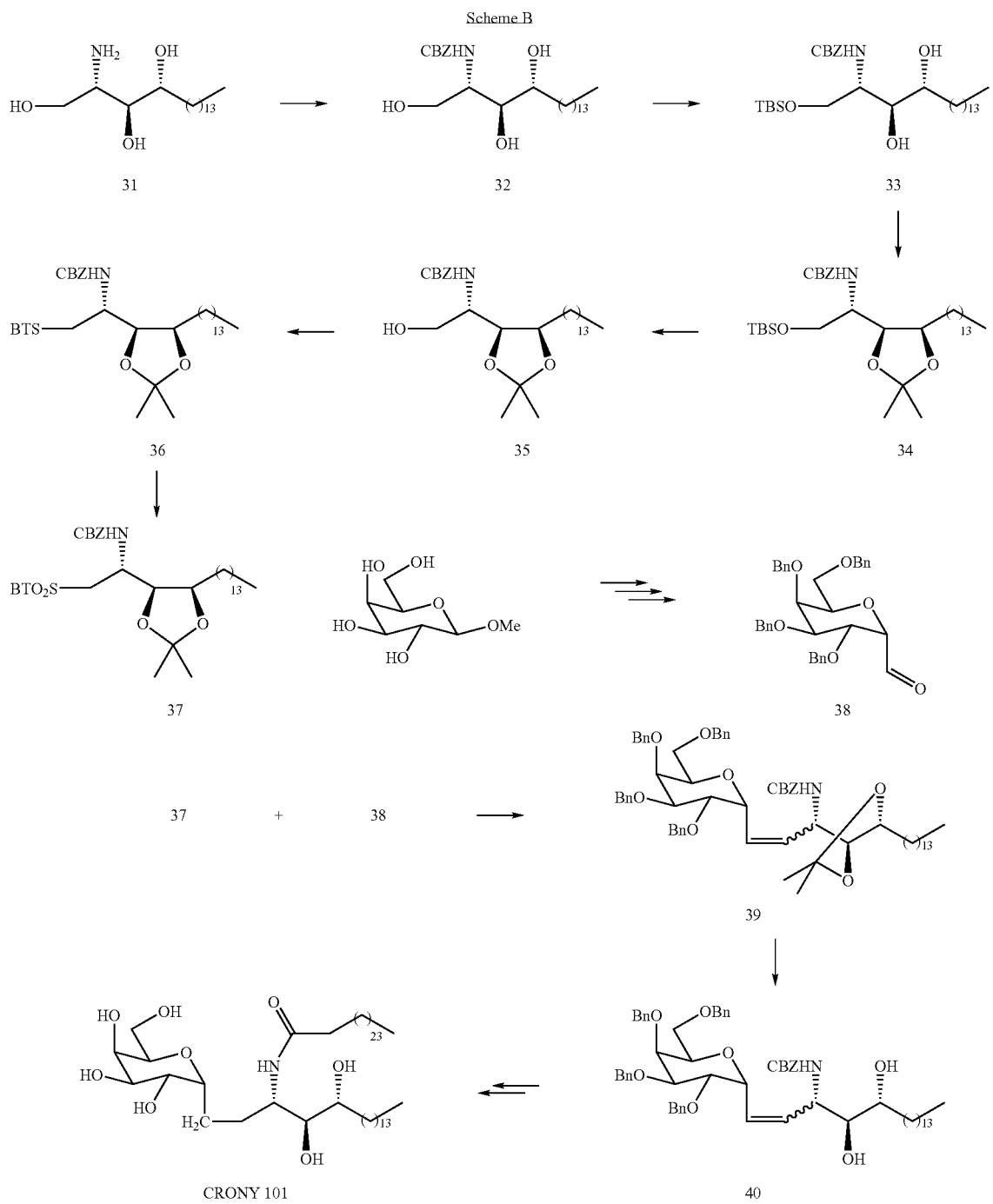

Scheme B

The following convergent approach to the synthesis of the C-glycoside analog of α-Galactosylceramide uses the one-pot Julia-Kocienski olefination, to couple the very sensitive sugar aldehyde with a similarly base-sensitive complete lipid sidechain. The sugar component was the α-C-galactosyl aldehyde 38, which was prepared according to the Bednarski procedure starting from methyl galactoside with an overall isolated yield of 40% after five steps. The lipid side chain was prepared from the commercially available phytosphingosine 31. The protection strategy was begun with benzyl carbamate formation, followed by selective silylation of the primary alcohol. After routine blocking the two secondary hydroxyl groups as an isopropylidene ketal, the primary hydroxy was released for Mitsunobo transformation to thioether. Oxidation of the sulfide 36 readily afforded sulfone 37 with an overall yield of 70% after six steps. The convergent coupling of 37 and 38 was carried out by employing the Julia-Kocienski olefination under an optimised condition to obtain 39 in 72% yield. Finally, removal of protecting groups and simultaneous reduction of the double bond according to standard procedures afford CRONY 101.

(2S,3R,4R)-2-amino-1,3,4-octadecanetriol (31)

(2S,3R,4R)-2-benzyloxycarbonylamino-1,3,4-octadecanetriol (32)

(Ozinskas et al., *J. Org. Chem.* 1986. 51: 4057-5050). To a suspension of starting material 31 (Cosmoferm B.V., Delft, Netherlands) (6.35 g, 20 mmol) in aqueous $NaHCO_3$ (1 N, 80 ml, 4 equiv.) and 1,4-dioxane (30 ml) was added benzyl chloroformate (3.31 ml, 1.1 equiv.). The reaction mixture was stirred at rt overnight, whereupon t.l.c (only ethyl acetate or DCM-MeOH 5:1) indicated the reaction was finished. The suspension was diluted with EtOAc and poured onto water. After separation, the aqueous phase was extracted with EtOAc (3×). The combined organic solutions were washed aqueous $NH_4Cl$, brine, dried over $Na_2SO_4$, and concentrated to afford a residue. The residue was purified by flash column chromatography (Petroether-EtOAc, 2:1 to only EtOAc) to provide compound 32 (8.13 g, 90%) as a white solid.

MS (ES, m/z): 452 $(M+H)^+$, 474 $(M+Na)^+$; $^1H$ NMR (500 MHz, $CDCl_3$) 7.39-7.35 (m, 5 H), 5.48 (d, J=7.3 Hz, 1 H), 5.02 (s, 2 H), 3.85-3.83 (m, 2 H), 3.71-3.67 (m, 1 H), 3.60-3.56 (m, 2 H), 3.09 (d, J=5.5 Hz, 1 H), 2.91 (m, 1 H), 2.40 (d, J=5.5 Hz, 1 H), 1.62-1.18 (m, 26 H), 0.79 (t, J=6.8 Hz, 3 H); $^{13}C$ NMR (75 MHz, $CDCl_3$) 153.2, 136.3, 128.5, 128.2, 128.0, 76.4, 73.1, 67.2, 62.2, 53.6, 33.3, 32.0, 29.8, 29.5, 25.9, 22.8, 14.2.

(2S,3R,4R)-1-O-tert-butyldimethyl-2-benzyloxycarbonylamino-1,3,4-octadecanctriol (33)

(Chaudhary et al., *Tetrahedron Letters*. 1979. 20: 99-102). To a solution of triol 32 (1.6 g, 3.54 mmol) in anhydrous DCM (25 ml) and DMF (5 ml) was added triethylamine (0.54 ml, 1.1 equiv.) at 0° C., followed by t-$BuMe_2SiCl$ (587 mg, 1.1 equiv.) and a catalytic amount of 4-DMAP (22 mg, 0.05 equiv.). After stirring for 1 h at the same temperature, the mixture was diluted with DCM and washed subsequently with water (2×), aqueous $NH_4Cl$ and brine. The organic phase was dried (sodium sulfate), concentrated and the residue purified by flash column chromatography (Petroether-EtOAc, 8:1 to 4:1) to provide diol 33 (1.92 g, 96%).

$^1H$ NMR (300 MHz, $CDCl_3$) 7.39-7.34 (m, 5 H), 5.46 (d, J=8.4 Hz, 1 H), 5.14 (s, 2 H), 3.99-3.91 (m, 2 H), 3.83-3.79 (m, 1 H), 3.67-3.61 (m, 2 H), 3.13 (d, J=7.7 Hz, 1 H), 2.64 (d, J=7.7 Hz, 1 H), 1.75-1.21 (m, 26 H), 0.93 (s, 9 H), 0.91 (t, J=9.9 Hz, 3 H), 0.13 (s, 3 H).

(2S,3R,4R)-1-O-tert-butyldimethyl-2-benzyloxycarbonylamino-3,4-Di-O-isopropylidene-1,3,4-octadecanetriol (34)

(Kitamura et al., *J. Am. Chem. Soc.* 1984. 106: 3252-3257). A solution of the diol 33 (3.33 g, 5.88 mmol) in dry DCM (60 ml) and 2,2-dimethoxypropane (6.0 ml, 8.0 equiv.) containing a catalytic amount of PPTs (50 mg) was stirred at room temperature for 3 h. The reaction mixture was diluted with DCM, quenched with aqueous $NaHCO_3$. After separation, the aqueous phase was extracted with DCM (3×). The combined organic solutions were washed with brine, dried over $Na_2SO_4$, and concentrated to afford acetonide 34. The residue was employed for the next step without further purification. MS (m/z): 606 $(M+H)^+$, 628 $(M+Na)^+$.

(2S,3R,4R)-2-benzyloxycarbonylamino-3,4-Di-O-isopropylidene-1,3,4-octadecanetriol (35)

(Corey et al., *J. Am. Chem. Soc.* 1984. 106: 3252-3257). To a solution of the residue silylether 34 in dry THF (80 ml) was added tetrabutylammoniumfloride (1.0 M in THF, 8 ml, 1.36 equiv.) under nitrogen at 0° C. After stirring for 1 h, saturated aqueous $NH_4Cl$ solution was added whereby the reaction was quenched. After separation, the aqueous phase was extracted with DCM (3×). The combined organic solutions were washed with aqueous $NaHCO_3$ and brine, dried over $Na_2SO_4$, concentrated, and the residue purified by flash column chromatography (Petroether-EtOAc, 2:1) to provide alcohol 35 (2.68 g, 92% for two steps) as a white solid.

MS (ES, m/z): 492 $(M+H)^+$, 514 $(M+Na)^+$; $^1H$ NMR (500 MHz, $CDCl_3$) 7.36-7.31 (m, 5 H), 5.17 (d, J=8.5 Hz, 1 H), 5.12 (d, J=12.2 Hz, 1 H), 5.08 (d, J=12.2 Hz, 1 H), 4.16 (m, 1 H), 4.11 (t, J=7.0 Hz, 1 H), 3.91-3.86 (m, 1 H), 3.84 (m, 1 H), 3.71 (m, 1 H), 2.19 (t, J=5.1 Hz, 1 H), 1.60-1.21 (m, 26 H), 1.45 (s, 3 H), 1.33 (s, 3 H), 0.88 (t, J=6.9 Hz, 3 H); $^{13}C$ NMR (75 MHz, $CDCl_3$) 155.8, 136.3, 128.4, 128.1, 127.9, 1, 78.0, 77.8, 67.0, 63.6, 51.9, 32.1, 29.9, 29.8, 29.7, 29.5, 29.5, 27.8, 26.8, 25.5, 22.8, 14.3.

2-[(3R,4R,5R)-3-benzyloxycarbonylamino-4,5-Di-O-isopropylidene-4,5-octadecanediolyl-thio]benzothiazole (36)

(Bellingham et al., *Synthesis* 1996, 285-296) A solution of DiPAD (0.56 ml, 2.84 mmol, 1.1 equiv) in dry THF (1 mL) was added to a solution of alcohol 35 (1.27 g, 2.58 mmol), $Ph_3P$ (747 mg, 2.2.84 mmol, 1.1 equiv.) and 2-mercaptanbenzothiazole (BTSH, 449 mg, 2.84 mmol, 1.1 equiv) in THF (80 ml) dropwise via syringe. After stirring for 2 h at ambient temperature, the mixture was diluted with DCM and poured onto sat. aq $NaHCO_3$. The phases were separated and the aqueous phase was extracted with DCM (3×). The combined organic solutions were washed subsequently with aqueous $NH_4Cl$, brine, and dried over $Na_2SO_4$. The filtrate was concentrated and the residue was purified by flash column chromatography (Petroether-EtOAc, 10:1 to 8:1) to provide thioether 36 (1.52 g, 92%) as a white solid.

MS (ES, m/z): 641 $(M+H)^+$, 663 $(M+Na)^+$; $^1H$ NMR (500 MHz, $CDCl_3$) 7.70 (d, J=8.1 Hz, 1 H), 7.64 (d, J=7.7 Hz, 1 H), 7.29 (t, J=7.5 Hz, 1 H), 7.20 (t, J=8.1 Hz, 1 H), 7.17 (br s, 3 H), 7.04 (br s, 2 H), 5.54 (d, J=6.5 Hz, 1 H), 4.93 (d, J=12.5 Hz, 1 H), 4.87 (d, J=12.5 Hz, 1 H), 4.09 (br s, 3 H), 3.70 (d, J=13.2 Hz, 1 H), 3.50 (m, 1 H), 1.55-1.16 (m, 26 H), 1.41 (s, 3 H), 1.25 (s, 3 H), 0.79 (t, J=6.8 Hz, 3 H).

2-[(3R,4R,5R)-3-benzyloxycarbonylamino-4,5-Di-O-isopropylidene-4,5-octadecanediolyl-sulfonyl]benzothiazole (37)

(Bellingham et al., *Synthesis* 1996, 285-296). To a solution of sulfide 36 (1.08 g, 1.69 mmol) in DCM (60 ml) was added $NaHCO_3$ (709 mg, 5 equiv.) and MCPBA (948 mg, 2.5 equiv.). The mixture was stired at ambient temperature overnight, whereupon t.l.c. indicated that the oxidation was complete. The mixture was diluted with DCM and quenched with aqueous sodium thiosulfate (20 ml, 10%). After pouring onto sat. aq $NaHCO_3$ and separation, the aqueous phase was extracted with DCM (3×). The combined organic extracts were dried over $Na_2SO_4$, concentrated, and the residue purified by flash column chromatography (Petroether-EtOAc-CHCl$_3$, 5:1:1) to provide sulfone 37 (1.08 g, 96%) as a white gel.

MS (ES, m/z): 673 (M+H)$^+$, 690 (M+NH$_4$)$^+$; $^1$H NMR (500 MHz, CDCl$_3$) 8.19 (d, J=7.9 Hz, 1 H), 7.97 (d, J=7.9 Hz, 1 H), 7.61 (t, J=7.6 Hz, 1 H), 7.57 (t, J=7.6 Hz, 1 H), 7.29 (br s, 3 H), 7.15 (br s, 2 H), 5.13 (d, J=8.8 Hz, 1 H), 4.86 (d, J=11.8 Hz, 1 H), 4.77 (d, J=11.9 Hz, 1 H), 4.31 (m, 1 H), 4.26 (m, 1 H), 4.13 (m, 1 H), 4.04 (dd, J=15.1, 8.1 Hz, 1 H), 3.93 (d, J=13.4 Hz, 1 H), 1.55 (s, 3 H), 1.51-1.21 (m, 26 H), 1.38 (s, 3 H), 0.88 (t, J=7.0 Hz, 3 H); $^{13}$C NMR (75 MHz, CDCl$_3$) 166.3, 154.9, 152.5, 136.8, 135.8, 128.4, 128.2, 128.1, 128.0, 127.8, 127.6, 125.4, 122.3, 108.3, 77.9, 77.2, 66.9, 55.7, 47.9, 32.0, 29.8, 29.7, 29.6, 29.6, 29.5, 28.8, 27.4, 26.8, 25.2, 22.8, 14.2:

(2,3,4,6-tetra-O-benzyl-α-D-galactopyranoside) methanal (38)

(Kobertz et al., *Tetrahedron Letters*. 1992. 33: 737-740. The α-C-galactosyl aldehyde 38 was prepared according to the Bednarski procedure starting from methyl galactoside with an overall isolated yield of 40% after five steps. $^1$H NMR (500 MHz, CDCl$_3$) 9.79 (s, 1 H), 7.38-7.17 (m, 20 H), 4.66-4.49 (m, 8 H), 4.33-4.30 (ddd, J=7.7, 4.4, 4.0 Hz, 1 H), 4.29 (d, J=4.4 Hz, 1 H), 4.12 (dd, J=6.2, 4.4 Hz, 1 H), 4.03 (dd, J=4.0, 2.6 Hz, 1 H), 3.87 (dd, J=10.6, 7.7 Hz, 1 H), 3.64 (dd, J=10.6, 4.4 Hz, 1 H), 3.62 (dd, J=6.6, 2.6 Hz, 1 H).

Julia Coupling to give 39 1-(2',3',4',6'-tetra-O-benzyl-α-D-galactopyranosyl)-3-benzyloxycarbonylamino-4,5-Di-O-isopropylidene-1-nonadecene-4,5-diol (39)

(Baudin et al., *Tetrahedron Letters* 1991 32: 1175-78; Blakemore et al., *Synlett* 1998, 26-28). To a solution of sulfone 37 (185 mg, 0.28 mmol, 1.3 equiv.) in dry THF (5 mL) at −60 to −70° C. was added dropwise NaHMDS (1.0 M in THF, 0.56 mL, 0.56 mmol, 2 equiv. based on sulfone) resulting in a bright yellow solution. After 45 min, the sugar aldehyde 38 (116 mg, 0.21 mmol) in THF (6 mL) was added dropwise via syringe pump in a period of 1 h. The mixture was stirred for 1 h at −60° C., 1 h at −42° C., then gradually warmed to −10° C. over 2 h. Stirring was continued for 1 h at rt before the reaction was quenched with water (10 mL) and diluted with Et$_2$O (10 mL). The phases were separated and the aqueous phase was extracted with Et$_2$O (3×). The combined organic phases were washed with water and brine, dried (Na$_2$SO$_4$) and concentrated. The residue was purified by flash chromatography (Petroether-EtOAc-CHCl$_3$, 7:1:1) to provide olefin 39 (152 mg, 72%) as yellow thick oil.

MS (ES, m/z): 1010 (M+H)$^+$, 1027 (M+NH$_4$)$^+$; E-9: $^1$H NMR (500 MHz, CDCl$_3$) 7.24-7.17 (m, 25H), 5.87 (dm, J=16.4 Hz, 1 H), 5.83 (dm, J=16.1 Hz, 1 H), 5.12 (d, J=12.5 Hz, 1 H), 5.06 (d, J=11.7 Hz, 1 H), 4.90 (d, J=9.2 Hz, 1 H), 4.81 (d, J=11.4 Hz, 1 H), 4.68-4.60 (m, 4 H), 4.59 (br s, 1 H), 4.56 (d, J=11.4 Hz, 1 H), 4.50 (d, J=12.1 Hz, 1 H), 4.42 (d, J=12.1 Hz, 1 H), 4.38 (m, 1 H), 4.14 (m, 1 H), 4.05-4.00 (m, 3 H), 3.95 (br s, 1H), 3.64 (m, 1 H), 3.57 (m, 2 H), 1.58-1.22 (m, 26 H), 1.36 (s, 3 H), 1.29 (s, 3 H), 0.88 (t, J=6.8 Hz, 3 H); Z-9: $^1$H NMR (500 MHz, CDCl$_3$) 7.22-7.13 (m, 25H), 6.24 (m, 1 H), 6.09 (m, 1 H), 5.87 (dd, J=11.5, 4.6 Hz, 1 H), 5.07 (d, J=12.5 Hz, 1 H), 5.00 (d, J=12.8 Hz, 1 H), 4.90 (br s, 1 H), 4.84 (d, J=11.4 Hz, 1 H), 4.77 (d, J=12.2 Hz, 1 H), 4.70 (d, J=12.1 Hz, 1 H), 4.63 (d, J=11.7 Hz, 1 H), 4.58 (d, J=11.7 Hz, 1 H), 4.52 (d, J=11.7 Hz, 1 H), 4.46 (br s, 2 H), 4.41 (d, J=12.1 Hz, 1 H), 4.31 (d, J=12.1 Hz, 1 H), 4.09 (m, 1 H), 3.94 (m, 1 H), 3.87 (m, 1 H), 3.80 (br s, 1H), 3.67-3.64 (m, 2 H), 3.29 (m, 1 H), 1.52-1.21 (m, 26 H), 1.40 (s, 3 H), 1.29 (s, 3 H), 0.88 (t, J=6.8 Hz, 3 H).

1-(2',3',4',6'-tetra-O-benzyl-α-D-galactopyranosyl)-3-benzyloxycarbonylamino-1-nonadecene-4,5-diol (40).

DiPAD=diisopropyl azodicarboxylate
MCPBA=meta chloroperbenzoic acid
PPTs=pyridinium p-toluenesulfonate
DCM=dichloromethane
THF=tetrahydrofuran
DMF=dimethylformamide The following Examples illustrate the invention without limiting its scope.

EXAMPLES

α-Galactosylceramide was synthesized by Kirin Brewery (Gumma, Japan). The stock solution was dissolved in a 0.5% polysorbate-20 (Nikko Chemical, Tokyo), 0.9% NaCl solution at a concentration of 200 µg/ml, and diluted in PBS just before injection into mice. α-C-galactosylceramide was synthesized as described herein. The stock solution was originally dissolved in 100% DMSO at a concentration of 1 mg/ml. Before injection into mice, it was diluted to a concentration of 200 µg/ml in a 0.5% polysorbate-20 (Nikko Chemical, Tokyo), 0.9% NaCl solution, and diluted in PBS just before injection into mice.

Six to eight-week-old female BALB/c mice were purchased from the National Cancer Institute (Bethseda, Md.). Six to eight-week-old female C57/BL6 mice were purchased from the Jackson Laboratory (Bar Harbor, Me.). CD1d-deficient mice and Jα18-deficient mice were obtained as gifts. IFN-γ-deficient mice of BALB/c background were purchased from the Jackson laboratory (Bar Harbor, Me.). IFN-γ-receptor-deficient mice were bred and maintained in an animal facility. IL-12p40-deficient mice of BALB/c and C57/BL6 background were purchased from the Jackson Laboratory (Bar Harbor, Me.). All mice were maintained under pathogen-free conditions.

*P. yoelii* (17NXL strain) was maintained by alternate cyclic passages in *Anopheles stephensi* mosquitoes and Swiss Wesbter mice. Sporozoites obtained from dissected salivary glands of infected mosquitoes 2 weeks after their infective blood were used for challenge of the mice. Challenge of mice to determine the development of liver-stage malaria infection was performed by an intravenous injection of 10,000 viable sporozoites into the tail vein. The outcome of the challenge was determined 40-42 hours later by measuring the parasite burden in the livers of the mice using a quantiative real-time RT-PCR method, as taught in Bruna-Romero et al., *Int. J. Parasitol.* 31, 1449-1502, 2001. Challenge of mice toe determine the development of blood stage malaria infection was performed by an intravenous injection of 75 viable sporozoites into the tail vein. Starting four days after challenge, daily peripheral blood smears were obtained from each mouse and examined miscroscopically for the presence of blood stage parasites until day 17 post-challenge. Mice were considered positive for parasitemia if at least one blood stage parasite was observed during the time of examination.

The degree of liver stage develiopment in challenged mice was determined by quantifying the amount of *P. yoelii*-specific 18S rRNA moelcules in the livers of the mice by way of the real-time RT-PCR technique of Bruna-Romero et al. A 2 µg sample of total RNA prepared from the livers of challenged mice was reverse-transcribed, and an aliquot of the resulting cDNA (133 ng) was used for real-time PCR amplification of *P. yoelii* 18S rRNA sequences. This amplification was performed in a GeneAmp® 5700 Sequence Detection System (PE Applied Biosystems, Foster City, Calif.). For this purpose, primers 5'-GGGGATTG-GTTTTGACGTTTTTGCG-3' (54 nM) and 5'-AAGCAT-TAAATAAAGCGAATACATCCTTAT-3' (60 nm) were used, together with the dsDNA-specific dye SYBR Green I incorporated into the PCR reaction buffer (PE Biosystems, Foster City, Calif.) in order to detect the PCR product generated. The temperature profile of the reaction was 95° C. for 10 minutes followed by 35 cycles of denaturation of 95° C. for 15 seconds and annealing/extension at 60° C. for 1 minute.

The development of melanoma lung metastases in C57/BL6 mice was determined by first challenging mice intravenously with $5 \times 10^4$ syngeneic B16 melanoma cells suspended in DMEM supplemented with 10% FCS. Two weeks after challenge the mice were sacrificed, the lungs removed, and the number of metastatic nodules counted, as described in Fujii et al., *Natl. Immunol.* 3, 867-874 (2002).

The serum concentrations of IFN-γ and IL-4 were measured 2, 6, 12, 24, 48, and 72 hours after treatment with α-GalCer, α-C-GalCer, or nothing by way of a sandwich ELISA (e-bioscience, San Diego). The serum concentrations of IL-12p70 were also measured at 2, 6, 12, 24, 48 and 72 hours after treatment by way of a sandwich ELISA (Pharmingen, San Diego).

Biological Data

As reported in Gonzalez-Aseguinolaza, *Proc. Nat'l Acad. Sci. USA* 97, 8461-8466 (2000) α-GalCer, when administered to mice two days before challenge with *Plasmodium* sporozoites, suppressed development of malaria liver stages in a manner dependent on both CD1d-restricted Vα14+ NKT cells and IFN-γ/IFN-γ receptor signaling. To see if α-C-GalCer exhibited a similar behavior, wild type mice were injected with either α-GalCer or α-C-GalCer two days before challenge with live *P. yoelii* sporozoites, and the degree of liver stage development was measured using a quantitative real time RT-PCR assay. Mice treated with either α-GalCer or α-C-GalCer showed virtually no liver stage development as compared to untreated control mice, proving that α-C-GalCer has in vivo anti-malaria activity similar to that of α-GalCer.

FIG. 1(A) demonstrates that α-C-GalCer displays anti-malaria activity. Wild type BALB/c mice were treated intraperitoneally with 2 µg of α-C-GalCer, α-GalCer or nothing two days before challenge with live *P. yoelii* sporozoites, and then checked for malaria liver stage development. The results are expressed as the average +/−SD of 5 mice.

Figure 1B:
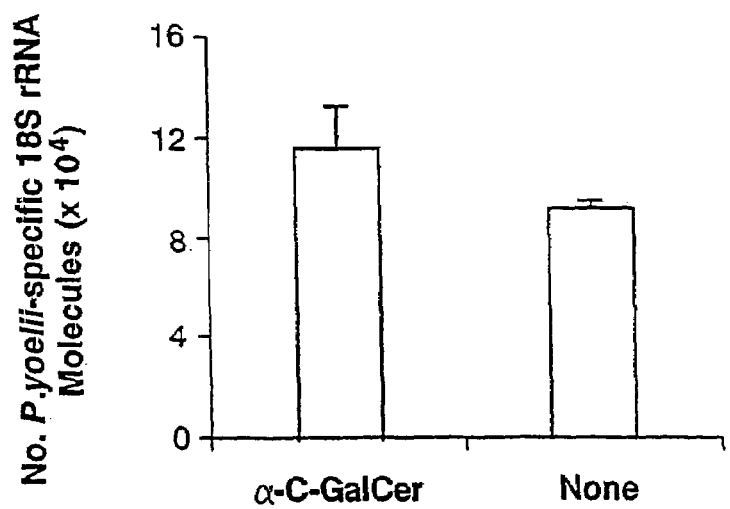
FIG. 1(B) is a bar graph showing malaria liver stage development in CD1d-deficient mice treated intraperitoneally with 2 μg of α-C-GalCer or nothing two days before challenge with sporozoites.

Thereafter, mice deficient in CD1d, Jα18 (formerly know as Jα281), IFN-γ, or IFN-γ receptor were injected with α-C-GalCer, and liver stage development was measured. As with α-GalCer, α-C-GalCer was unable to suppress *P. yoelii* liver stages in the absence of these molecules (FIGS. 1B and C). FIGS. 1(B) and (C) demonstrate that α-C-GalCer's anti-malaria activity requires CD1d molecules and Vα14+ NKT cells. CD1d- or Jα18-deficient mice were tereated intraperitoneally with 2 µg of α-C-GalCer, α-GalCer or nothing two days before challenge with live *P. yoelii* sporozoites, and then checked for malaria liver stage development. The results are expressed as the average +/−SD of 5 mice.

Figure 2A:
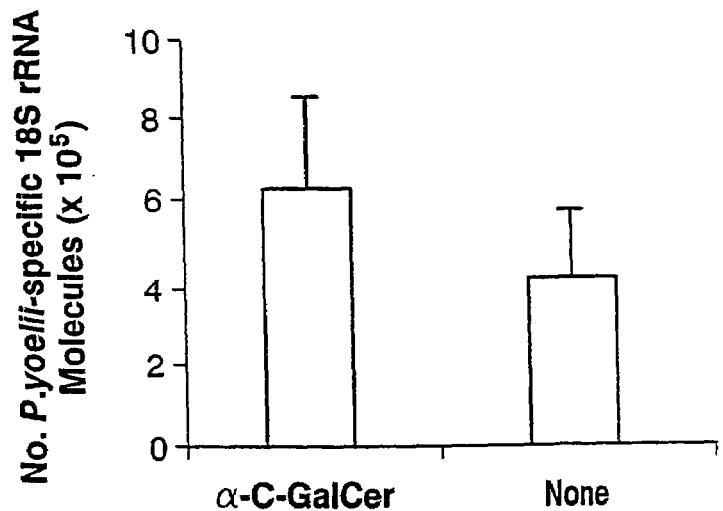
FIGS. 2(A) and (B) are bar graphs showing malaria liver stage development in IFN-γ (FIG. 2(A)) and IFN-γ receptor (FIG. 2(B)) deficient mice treated intraperitoneally with 2 μg of α-C-GalCer or nothing two days before challenge with sporozoites.

FIGS. 2(A) and (B) demonstrate that α-C-GalCer's anti-malaria activity requires IFN-γ/IFN-γ receptor. IFN-γ- or IFN-γ receptor-deficient mice were treated intraperitoneally with 2 µg of either α-C-GalCer, α-GalCer or nothing two days before challenge with sporozoites, and then checked for malaria liver stage development. The results are expressed as the average +/−SD of mice.

Figure 1C:
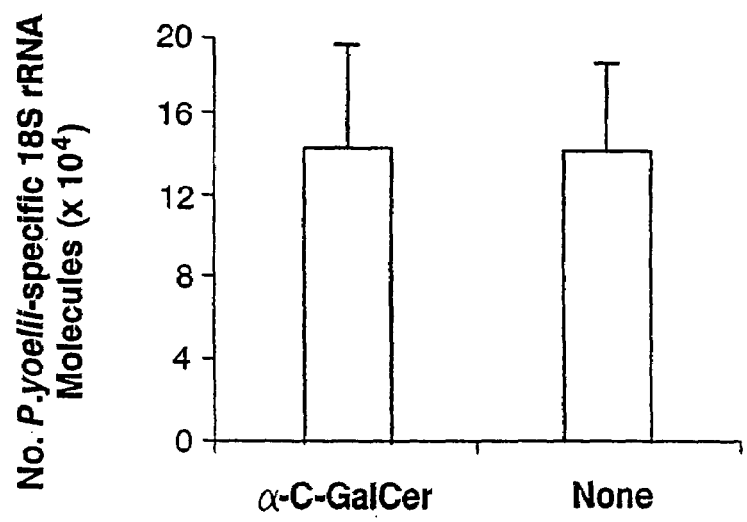
FIG. 1(C) is a bar graph showing malaria liver stage development in Jα18-deficient mice treated intraperitoneally with 2 μg of α-C-GalCer or nothing two days before challenge with sporozoites.
Figure 2B:
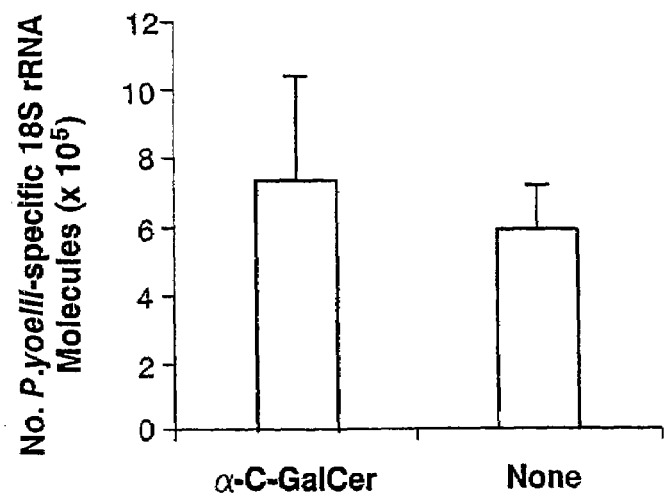

In FIGS. 1 and 2 the data represent one or two or more experiments with similar results.

Since both CD1- and Jα18-deficient mice lack Vα14 NKT cells, the results show that α-C-GalCer is a ligand for this cell type in vivo. Moreover, the requirement of IFN-γ/IFN-γ receptor signaling indicates that α-C-GalCer stimulates a Th1-type response.

The above data indicate that no pharmacodynamic difference in anti-malaria activity exists between α-C-GalCer and α-GalCer. To measure pharmacokinetic differences, the dose response and kinetic effect of the of α-GalCer and α-C-GalCer against malaria were measured. For the dose response, mice were treated with α-GalCer or α-C-GalCer three days before *P. yoelii* sporozoite challenge, and then liver stage development was measured. α-C-GalCer was found to exhibit a much more potent anti-malaria activity, with a dose of 1 ng α-C-GalCer equal to a dose of 1 µg α-GalCer.

Figure 3A:
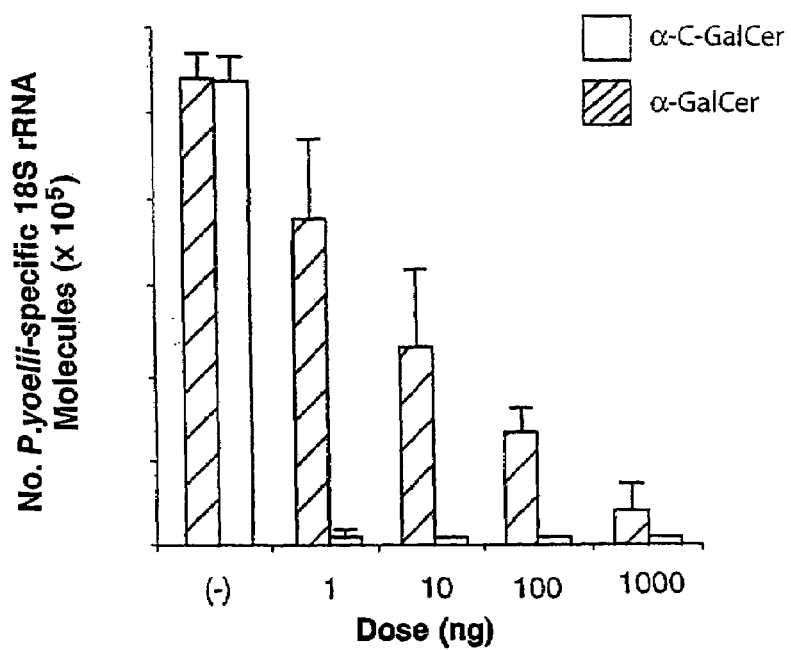
FIG. 3(A) is a bar graph showing malaria liver stage development in wild type BALBc mice treated intraperitoneally with different doses of (□) α-C-GalCer or (▨) α-GalCer three days before challenge with live P. yoelii sporozoites.

In FIG. 3(A) α-C-GalCer displayed a more potent anti-malaria response than α-GalCer. Wild type BaLB/c mice were treated intraperitoneally with different doses of either α-C-GalCer (□) or α-GalCer (▨) 3 days before challenge with live *P. yoelii* sporozoites, and then checked for malaria liver stage development. The results are expressed as the average +/−SD of 5 mice.

Figure 3B:
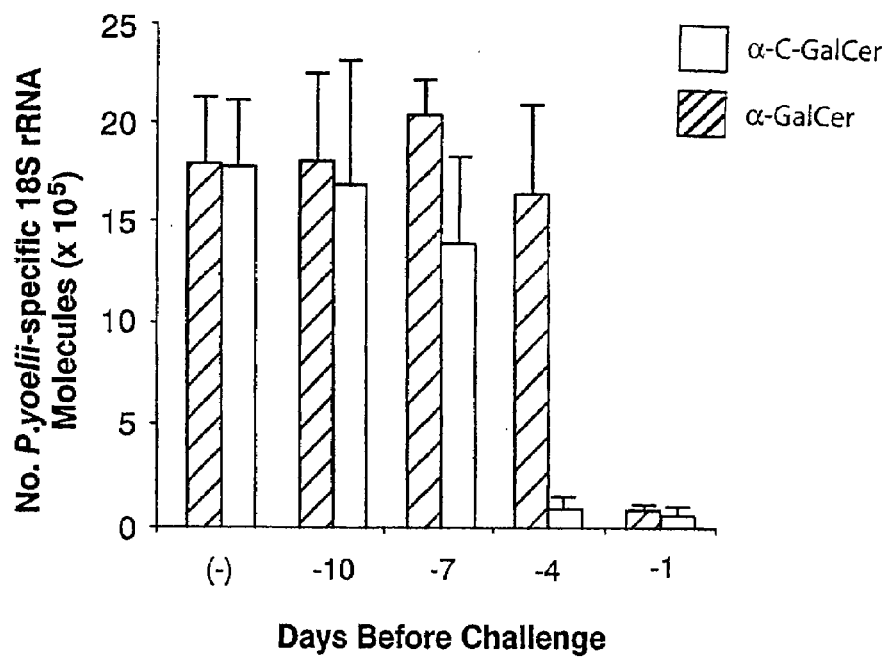
FIG. 3(B) is a bar graph showing malaria liver stage development in wild type BALBc mice treated intraperitoneally with 100 ng of (□) α-C-GalCer or (▨) α-GalCer at various times before challenge with sporozoites.

To measure the kinetic effect, mice were treated with an identical dose of α-GalCer or α-C-GalCer at different time points prior to sporozoite challenge, and the liver stages were measured. α-C-GalCer exhibited an extended anti-malaria effect of up to three days longer than α-GalCer (FIG. 3(B)).

FIG. 3(B) shows wild type BALB/c mice treated intrepertioneally with 100 ng of either α-C-GalCer (□) or α-GalCer (▨) at various times before challenge with sporozoites, and then checked for malaria liver stage development. The results are expressed as the average +/−SD of five mice.

Figure 3C:
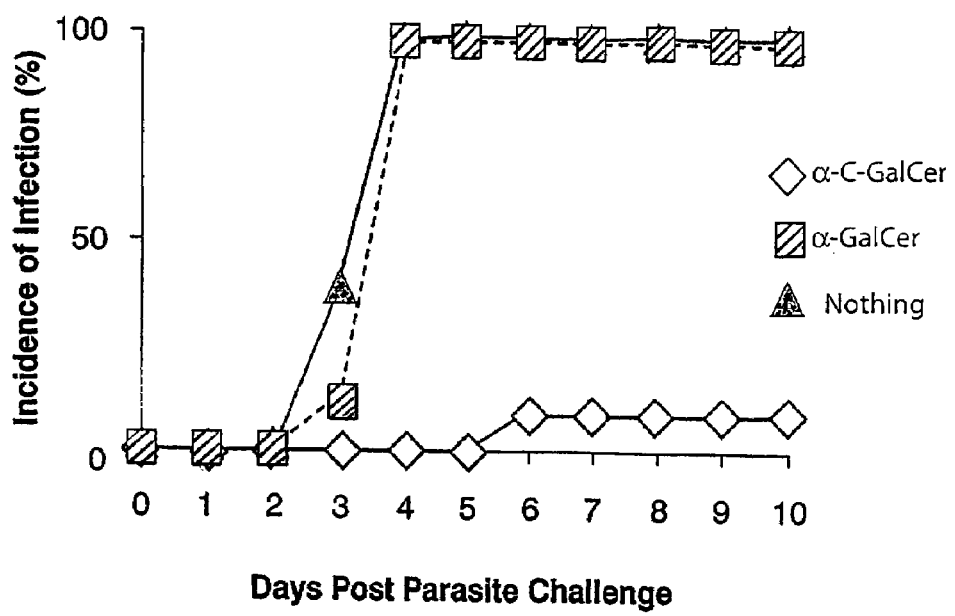
FIG. 3(C) is a graph showing incidence of infection in wild type BALBc mice treated intraperitoneally with 100 ng of (◇) α-C-GalCer, (▨) α-GalCer or (▲) nothing 3 days before challenge with live P. yoelli sporozoites. Mice where then monitored daily for the presence of blood stage parasites.

To confirm this superior anti-malaria effect of α-C-GalCer, the ability of either glycolipid to prevent blood stage malaria infection in mice challenged with live sporozoites was assessed. As shown below in FIG. 3(C), α-C-GalCer was shown to better protect mice from sporozoite-induced blood stage malaria infection than α-GalCer. Wild type BALB/c mice were injected intraperotineally with 100 ng of α-C-GalCer (◇), α-GalCer (▨) or nothing (▲) three days before challenge with live *P. yoelii* sporozoites. Mice were then monitored daily for the presence of blood stage parasites. α-C-GalCer completely protected 9 of 10 mice from blood stage malaria, while an identical dose of α-GalCer protected 0 of 10 mice, the same outcome as untreated controls. Since blood stage infection requires prior successful development of the liver stages, the enhanced activity of α-C-GalCer against both liver and blood stage infections is consistent and demonstrates the superior effect of α-C-GalCer in vivo.

Since NKT cell-mediated protection against malaria requires IFN-γ/IFN-γ receptor signaling, the enhanced activity with α-C-GalCer suggests it might be superior in other disease models requiring Th1-type responses for control. One such model involves melanoma metastases to the lungs, in which α-C-GalCer-mediated inhibition requires an IFN-γ response initiated by NKT cells (Smyth et al., *Blood* 99, 1254-1266 (2002)). To determine whether α-C-GalCer is better able to control such metastases than α-GalCer, mice were injected with various doses of α-GalCer and αC-GalCer two days before challenge with melanoma cells, and two weeks later we checked the lungs for the number of metastatic nodules that had developed. α-C-GalCer exhibited a much more potent anti-cancer response than α-GalCer, with 1 ng α-C-GalCer equal to 100 ng of α-GalCer.

Figure 4:
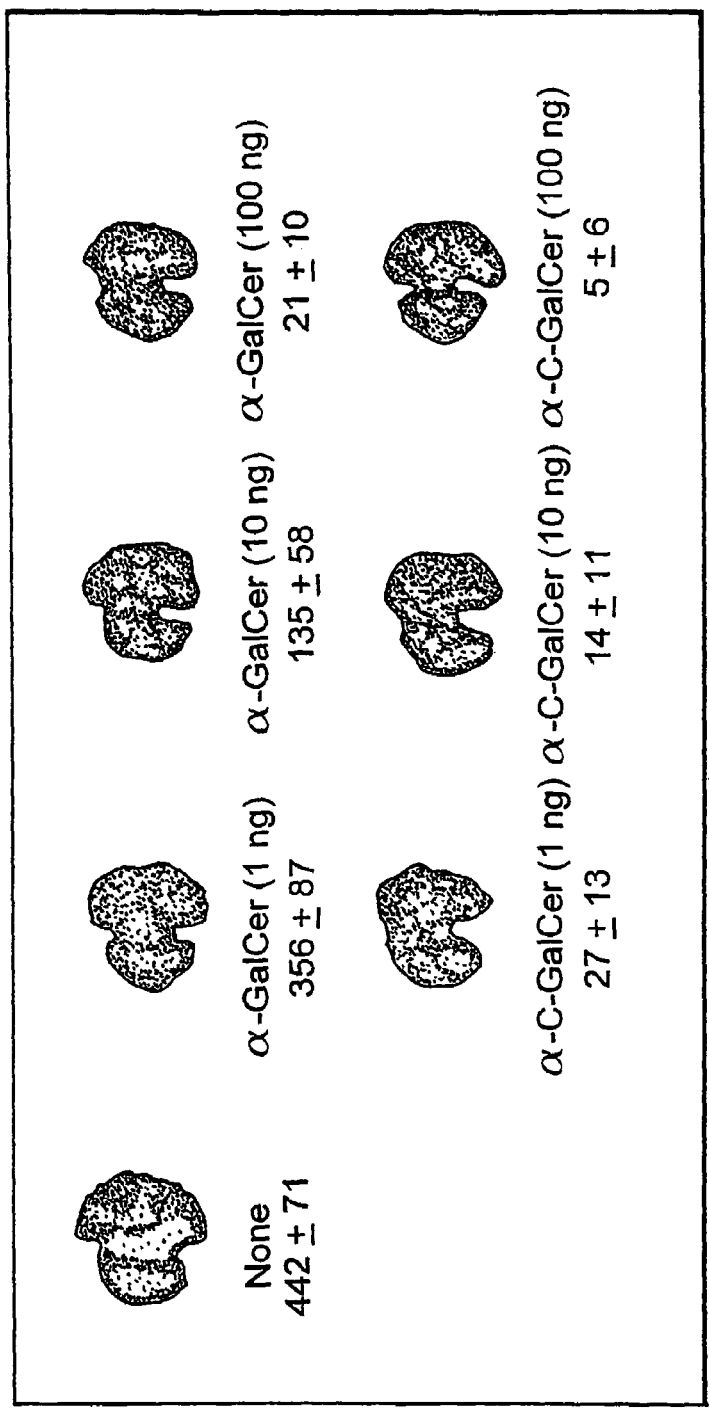
FIG. 4 depicts the lungs of C57BL/6 mouse treated intravenously with different doses of α-C-GalCer or α-GalCer two days before intravenous challenge with 5×10⁴ syngeneic B16 melanoma cells. The results in the study are expressed as the average number of metastatic nodules thta had developed in the lungs +/−SD of five mice.

In FIG. 4, wild type C57BL/6 mice were treated intravenously with different doses of either α-C-GalCer or α-GalCer two days before intravenous challenge with 5×10$^4$ syngeneic B16 melanoma cells. Two weeks later, the lungs were checked for tumor metastases. The results are expressed as the average +/−SD of 5 mice. The pictures shown come from one representative mouse out of five per group. These results clearly show a superior anti-cancer effect for α-C-GalCer, and further support the hypothesis that α-C-GalCer stimulates a preferential Th1-type response in vivo.

Optimal IFN-γ production by NKT cells requires antigen presenting cell (APC)-derived IL-12 (Kitamura et al, *J. Exp. Med.* 189, 1121-1128 (1999); Tomura et al. *J. Immunol.* 163, 93-101 (1999); Yang, *Int. Immunol.* 12, 1669-1675 (2000). Since α-C-GalCer stimulates much greater IL-12 production than α-GalCer, tests were conducted to determine if IL-12 is necessary for the difference between α-C-GalCer and α-GalCer. As expected, in wild type mice α-C-GalCer suppressed liver stage development to a much greater degree than α-GalCer (FIG. 6(A)); however, in IL-12 deficient mice there was no difference in anti-malaria activity between α-GalCer and α-C-GalCer (FIG. 6(B)). The data suggests that IL-12 is a key factor driving the difference between α-GalCer and α-C-GalCer. It is possible that α-C-GalCer stimulates more IL-12 production by APCs, either by way of its direct interaction with the APCs or via the signalling that results from the interaction of the NKT cell TCR with APC CD1d/glycolipid complex. Increased IL-12 would result in enhanced IFN-γ and decreased IL-4 production by NKT cells (Ogarra, *Trends Cell Bio.* 10, 542550 (2000); Elser, *Immunity* 17, 703-712 (2002), as well as enhanced IFN-γ production by other cell types, notably NK cells Eberl, *Eur. J. Immunol.* 30, 985-992 (2000). The observation that α-C-GalCer stimulates increased IFN-γ and decreased IL-4 production is consistent with its stimulation of increased IL-12. This also helps explain the enhanced potency and kinetic effect of α-C-GalCer against malaria and melanoma. However, additional properties likes a longer in vivo half-life of the molecule cannot be ruled out as alternative explanations.

Figure 5B:
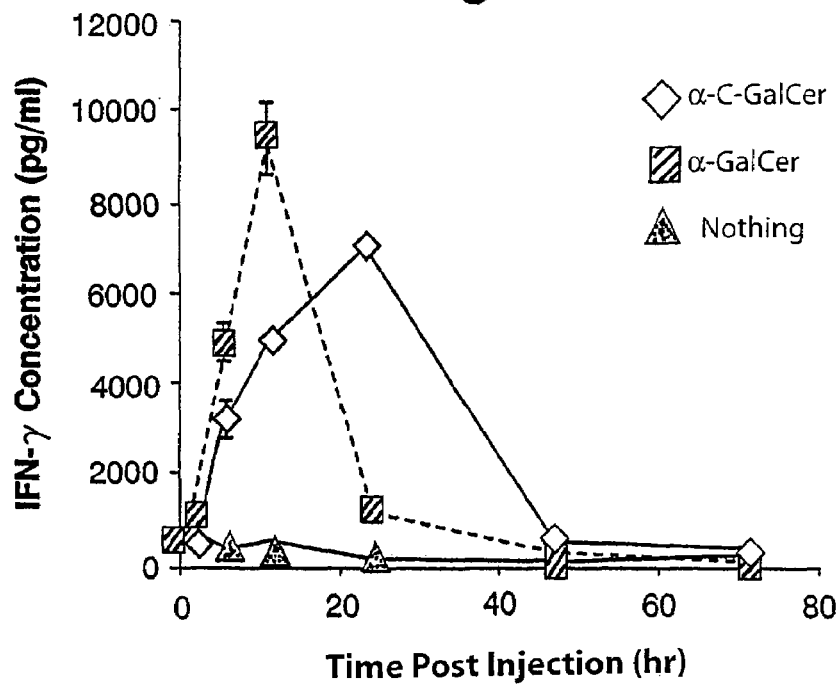
FIGS. 5(A), (B) and (C) are graphs showing cytokine production in wild type BALB/c mice treated intravenously with 1 μg of α-C-GalCer (◇) or α-GalCer (▨) or with nothing (▲). Serum samples were obtained at the indicated time points (hr) after injection for ELISA analyses of IL-4 (FIG. 5(A)), IFN-γ (FIG. 5(B)), and IL-12 (FIG. 5(C)) concentrations.
Figure 5C:
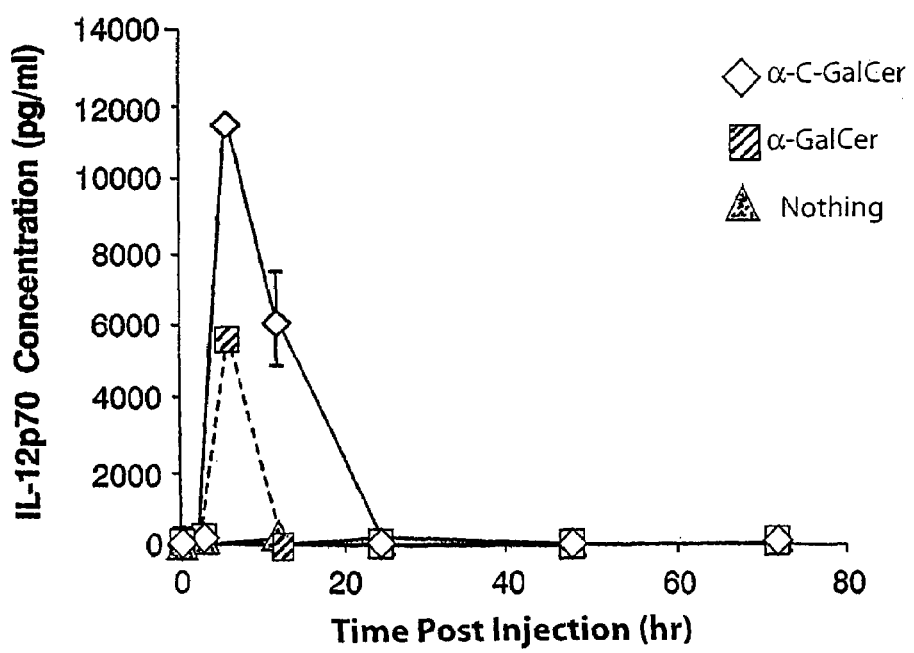

In FIG. 5, wild type BALB/c mice were treated intravenously with 1 μg of either α-C-GalCer (◇) or α-GalCer (▨) or with nothing (▲), and serum samples were obtained at the indicated time points after injection of ELISA analyses of IL-4 (FIG. 5(A)), IFN-γ (FIG. 5(B)), and IL-12 (FIG. 5(C)) concentrations. The data are expresed as the average +/−SD of two different dilutions of pooled sera.

Figure 6A:
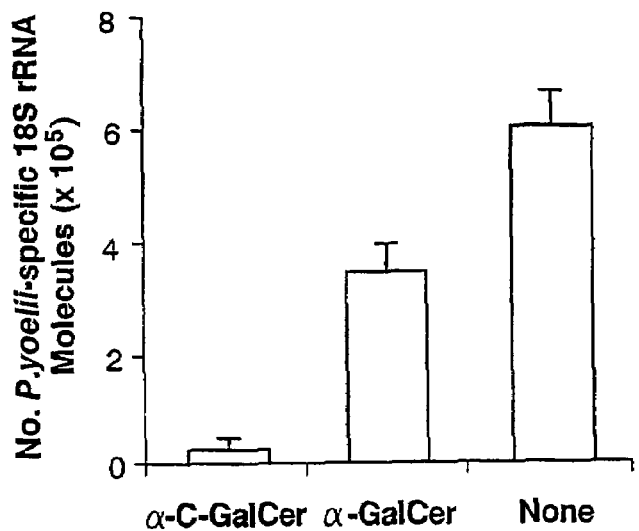
FIGS. 6(A) and (B) are bar graphs showing malaria liver stage development in wild type (FIG. 6(A)) or IL-12-deficient (FIG. 6(B)) mice treated intraperitoneally with 100 ng of α-C-GalCer or α-GalCer or with nothing four days before challenge with live P. yoelii sporozoites.
Figure 6B:
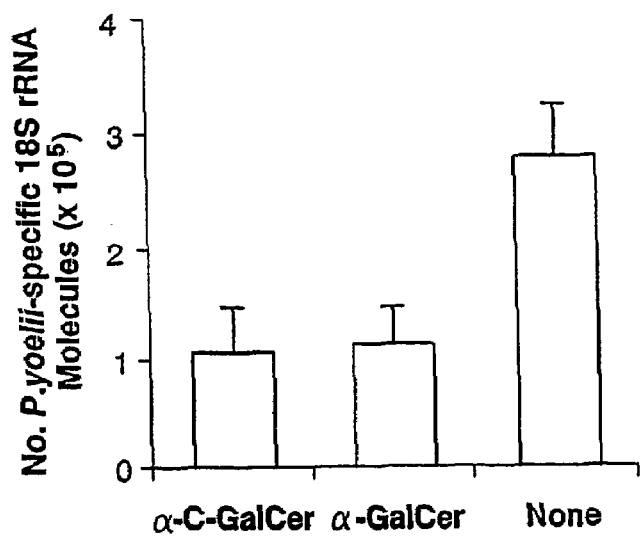

In FIG. 6, α-C-GalCer's enhanced anti-malaria effect is abrogated in the absence of IL-12. Wild type (FIG. 6(A)) or IL-12-deficient (FIG. 6(B)) mice were treated intraperitoneally with 100 ng of α-C-GalCer, α-GalCer or nothing four days before challenge with live *P. yoelii* sporozoites, and then checked for malaria liver stage development. The results are expressed as the average +/−SD of 5 mice.

To see if α-C-GalCer does indeed stimulate a preferential Th1-type response in vivo, mice were injected with the same dose of either α-C-GalCer or α-GalCer, and at various time points afterwards blood samples were obtained for ELISA analyses of IFN-γ, IL-4, and IL-12 concentrations in the sera. For IL-4, both α-C-GalCer or α-GalCer stimulated peak concentrations 2 hours after treatment; however, α-GalCer stimluated concentrations roughly 3 times higher than α-C-GalCer (FIG. 5(A)). For IFN-γ, both α-C-GalCer and α-GalCer stimulated detectable levels starting at 6 hours, but α-GalCer's peak occurred 12 hours post-treatment, returning to baseline by 24 hours. In contrast, α-GalCer's peak occurred 24 hours post-treatment, returning to baseline by 48 hours (FIG. 5(B)). Finally, for IL-12, both α-C-GalCer and α-GalCer stimulated peak concentrations 6 hours after treatment; howver, α-C-GalCer stimulated concentrations 2 times higher than α-GalCer. Moreover, α-C-GalCer continued stimulating detectable IL-12 levels 12 hours after treatment, whereas at this time point α-GalCer stimluated IL-12 levels were undetectable (FIG. 5(C)). Thus, over time α-C-GalCer stimluated enhanced levels of the Th1 cytokines IL-12 and IFN-γ, and diminished levels of the Th2 cytokine IL-4 as compared to α-GalCer, showing that, in vivo, it does indeed stimulate a preferential Th1-type response.

The data show that α-C-GalCer acts as a NKT cell ligand in vivo, and that it stimulates a preferential Th1-type response compared to α-GalCer. Due to the consumed nature of NKT cell responses in mammals, it is likely that α-C-GalCer, which stimulates Vα14+NKT cells in mice, also stimulates Vα14+NKT in humans (Brossay, et al., *J. Exp. Med.* 188, 1521-1528 1998)). As a result α-C-GalCer's Th-1 polarizing activity means it is an excellent chemotherapeutic candidate for a number of human diseases, including cancer, allergy and various infectious diseases such as hepatitis B and C.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

All patents, applications, publications, test methods, literature, and protocols cited throughout this application, are incorporated herein by reference entireties for all purposes. In case of a conflict between material incorporated by reference and the present specification, the present specification controls.

What is claimed is:

1. A method of inducing the production of Th1 type cytokines in a mammal suffering from a disease that is treatable by inducing TH1 type responses, by administering to said mammal a therapeutically effective amount of a compound of formula I

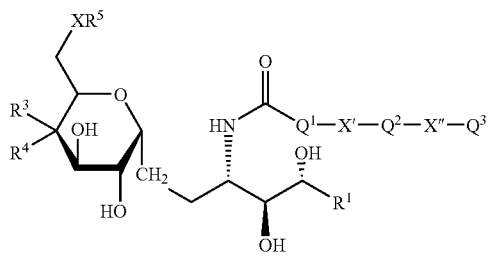

wherein X is O or NH;
- $R^1$ is selected from the group consisting of —$(CH_2)_{11}$CH$_3$, —$(CH_2)_{12}$CH$_3$, —$(CH_2)_{13}$CH$_3$, —$(CH_2)_9$CH$(CH_3)_2$, —$(CH_2)_{10}$CH$(CH_3)_2$, —$(CH_2)_{11}$CH$(CH_3)_2$ and $(CH_2)_{11}$CH$(CH_3)$—$C_2H_5$;
- $R^3$ is OH or a monosaccharide and $R^4$ is hydrogen, or $R^3$ is hydrogen and $R^4$ is OH or a monosaccharide;
- $R^5$ is hydrogen or a monosaccharide;
- $Q^1$ is optionally present and is a $C_{1-10}$ straight or branched chain alkylene, alkenylene, or alkynylene;
- X' is optionally present and is O, S or NR$^8$;
- $Q^2$ is optionally present and is a $C_{1-10}$ straight or branched chain alkylene, alkenylene or alkynylene;
- X" is optionally present and is O, S or NR$^8$;
- $Q^3$ is a straight or branched chain $C_{1-10}$ alkyl, alkenyl or alkynyl, or is hydrogen, wherein each $Q^1$, $Q^2$ or $Q^3$ is optionally substituted with hydroxyl, halogen, cyano, nitro, SO$_2$, NHR$^8$, or C(=O)—R$^9$; and wherein
- $R^8$ is hydrogen, $C_{1-5}$ alkyl, $C_{1-5}$ alkoxy, halogen, cyano, nitro, SO$_2$ or C(=O)—R$^9$;
- $R^9$ is hydrogen, $C_{1-5}$ alkyl, $C_{1-5}$ alkoxy or NHR$^{10}$;
- $R^{10}$ is hydrogen, $C_{1-5}$ alkyl or $C_{1-5}$ alkoxy;

and a pharmaceutically acceptable salt or ester thereof, wherein the compound does not induce substantial production of interleukin 4 (IL-4).

2. The method of claim 1, wherein said Th1 type cytokines comprise interferon-γ (IFN-γ) and interleukin 12 (IL-12).

3. The method of claim 1, wherein the mammal is human.

4. The method of claim 1, wherein the disease is an infectious disease selected from the group consisting of malarial infection, HIV infection, hepatitis B virus infection, hepatitis C virus infection, *Mycobacterium* infection, respiratory syncitial virus infection, and Herpes virus infection.

5. The method of claim 1, wherein the disease is allergy.

6. The method of claim 1, wherein the disease is asthma.

7. The method of claim 1, wherein the disease is sarcoidosis.

8. The method of claim 1, wherein the disease is a cancer selected from the group consisting of carcinoma of bladder, breast, colon, esophagus, liver, lung, ovary, pancreas, prostate, kidney, renal, stomach, testicles, cervix, thyroid, skin, squamous cell carcinoma, small cell lung cancer, non-small cell lung cancer, leukemia, acute lymphocytic leukemia, acute lymphoblastic leukemia, T cell lymphoma, B cell lymphoma, Hodgkin's lymphoma, non-Hodgkin's lymphoma, hairy cell lymphoma, Burkett's lymphoma, acute myelogenous leukemia, chronic myelogenous leukemia, myelodysplastic syndrome, promyelocytic leukemia, fibrosarcoma, rhabdomyosarcoma, astrocytoma, neuroblastoma, glioma, schwannoma, seminoma, teratocarcinoma, osteosarcoma, xenoderoma pigmentosum, keratoctanthoma, thyroid follicular cancer, and Kaposi's sarcoma.

9. The method of claim 1, wherein the disease is melanoma.

* * * * *

UNITED STATES PATENT AND TRADEMARK OFFICE
CERTIFICATE OF CORRECTION

PATENT NO. : 7,273,852 B2 Page 1 of 1
APPLICATION NO. : 10/462211
DATED : September 25, 2007
INVENTOR(S) : Moriya Tsuji et al.

It is certified that error appears in the above-identified patent and that said Letters Patent is hereby corrected as shown below:

Title Page, Item (73) Assignee:

Please insert --New York University--

Signed and Sealed this

Twenty-first Day of October, 2008

JON W. DUDAS
*Director of the United States Patent and Trademark Office*